United States Patent
Chen et al.

(10) Patent No.: US 10,495,778 B2
(45) Date of Patent: Dec. 3, 2019

(54) SYSTEM AND METHODS FOR CROSS-TOOL OPTICAL FLUID MODEL VALIDATION AND REAL-TIME APPLICATION

(71) Applicant: Halliburton Energy Services, Inc., Houston, TX (US)

(72) Inventors: Dingding Chen, Tomball, TX (US); Bin Dai, Spring, TX (US); Christopher Michael Jones, Houston, TX (US); Darren Gascooke, Houston, TX (US); Tian He, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 15/124,282

(22) PCT Filed: Nov. 19, 2015

(86) PCT No.: PCT/US2015/061487
§ 371 (c)(1),
(2) Date: Sep. 7, 2016

(87) PCT Pub. No.: WO2017/086961
PCT Pub. Date: May 26, 2017

(65) Prior Publication Data
US 2017/0261640 A1    Sep. 14, 2017

(51) Int. Cl.
*G01N 33/24* (2006.01)
*G01V 8/02* (2006.01)
(Continued)

(52) U.S. Cl.
CPC .............. *G01V 8/02* (2013.01); *E21B 47/102* (2013.01); *E21B 49/08* (2013.01); *G01N 33/18* (2013.01);
(Continued)

(58) Field of Classification Search
CPC ........ G01V 8/02; G06N 3/04; G06F 17/5009; G01N 33/18; G01N 33/2823; G01N 33/241; G01N 33/225; E21B 47/102; E21B 49/08
See application file for complete search history.

(56) References Cited

U.S. PATENT DOCUMENTS

| | | |
|---|---|---|
| 4,866,644 A | 9/1989 | Shenk et al. |
| 6,549,861 B1 | 4/2003 | Mark et al. |

(Continued)

FOREIGN PATENT DOCUMENTS

| | | | |
|---|---|---|---|
| WO | 2002066791 A1 | 8/2002 | |
| WO | WO 2013089764 A1 * | 6/2013 | ........... G01N 33/241 |
| WO | 2014137354 A1 | 9/2014 | |

OTHER PUBLICATIONS

ISR/WO for PCT/US2015/061487 dated Aug. 18, 2016.

*Primary Examiner* — Jarrett J Stark
(74) *Attorney, Agent, or Firm* — Gilliam IP PLLC

(57) ABSTRACT

A method of cross-tool optical fluid model validation includes selecting verified field data measured with a first sensor of an existing tool as validation fluids and selecting a second sensor for a new tool or on a different existing tool. The method may also include applying cross-tool optical data transformation to the validation fluids in a tool parameter space from the first sensor to the second sensor, and calculating the synthetic optical responses of the second sensor on the validation fluids through cross-space data transformation. The method may further include determining a new or adjusting an existing operational fluid model of the second sensor in a synthetic parameter space according to the candidate model performance evaluated on the validation fluids, and optimizing well testing and sampling (Continued)

operation based on real-time estimated formation fluid characteristics using the validated fluid models of the second sensor in an operating tool.

22 Claims, 14 Drawing Sheets

(51) Int. Cl.

| | |
|---|---|
| E21B 49/08 | (2006.01) |
| E21B 47/10 | (2012.01) |
| G01N 33/18 | (2006.01) |
| G01N 33/22 | (2006.01) |
| G01N 33/28 | (2006.01) |
| G06F 17/50 | (2006.01) |
| G06N 3/04 | (2006.01) |

(52) U.S. Cl.
CPC ......... *G01N 33/225* (2013.01); *G01N 33/241* (2013.01); *G01N 33/2823* (2013.01); *G06F 17/5009* (2013.01); *G06N 3/04* (2013.01)

(56) References Cited

U.S. PATENT DOCUMENTS

| | | | |
|---|---|---|---|
| 6,732,052 B2 | 5/2004 | Macdonald et al. | |
| 7,362,422 B2 | 4/2008 | DiFoggio et al. | |
| 7,966,273 B2 | 6/2011 | Hegeman et al. | |
| 8,093,893 B2 | 1/2012 | Niemeyer et al. | |
| 8,285,531 B2 | 10/2012 | Moran et al. | |
| 8,417,495 B2 | 4/2013 | Dashevskiy | |
| 2005/0263281 A1* | 12/2005 | Lovell .................. | E21B 47/123 166/255.1 |
| 2007/0035737 A1* | 2/2007 | Andrews ............ | G01N 21/3577 356/436 |
| 2008/0034025 A1 | 2/2008 | Zubkov et al. | |
| 2008/0128134 A1* | 6/2008 | Mudunuri ................ | C10G 1/02 166/302 |
| 2009/0059332 A1* | 3/2009 | DiFoggio ............ | G01N 21/0303 359/196.1 |
| 2009/0071652 A1* | 3/2009 | Vinegar .................. | E21B 36/04 166/303 |
| 2009/0166085 A1* | 7/2009 | Ciglenec ................ | E21B 49/08 175/24 |
| 2009/0189617 A1* | 7/2009 | Burns .................... | E21B 43/24 324/649 |
| 2009/0260823 A1* | 10/2009 | Prince-Wright ....... | C10G 21/22 166/302 |
| 2012/0158305 A1* | 6/2012 | Rodney .................... | G01V 3/26 702/6 |
| 2012/0224455 A1* | 9/2012 | Dorovsky .............. | G01V 11/00 367/35 |
| 2013/0110486 A1* | 5/2013 | Polyakov ................ | E21B 49/00 703/10 |
| 2013/0116926 A1* | 5/2013 | Rodney .................. | G01V 1/42 702/8 |
| 2013/0312481 A1 | 11/2013 | Pelletier et al. | |
| 2014/0204121 A1* | 7/2014 | Whitley .................. | G06T 11/00 345/633 |
| 2014/0293282 A1* | 10/2014 | Indo ........................ | E21B 49/08 356/402 |
| 2014/0352397 A1* | 12/2014 | Smits ..................... | E21B 49/10 73/1.02 |
| 2015/0186574 A1* | 7/2015 | Huang .................... | E21B 7/061 703/7 |
| 2016/0178785 A1* | 6/2016 | Wilson .................... | E21B 49/08 324/324 |
| 2016/0320527 A1* | 11/2016 | Chen ........................ | E21B 7/00 |

\* cited by examiner

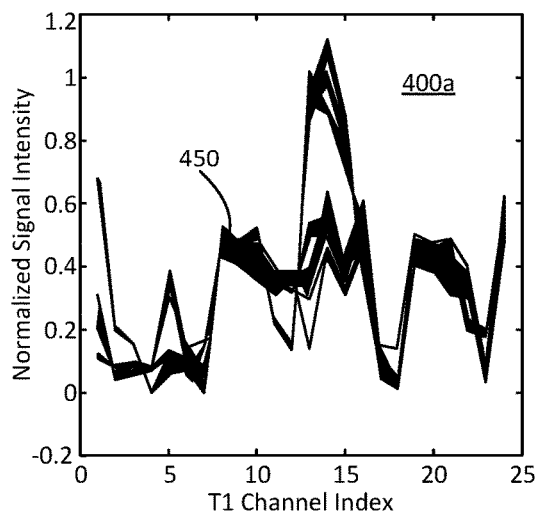
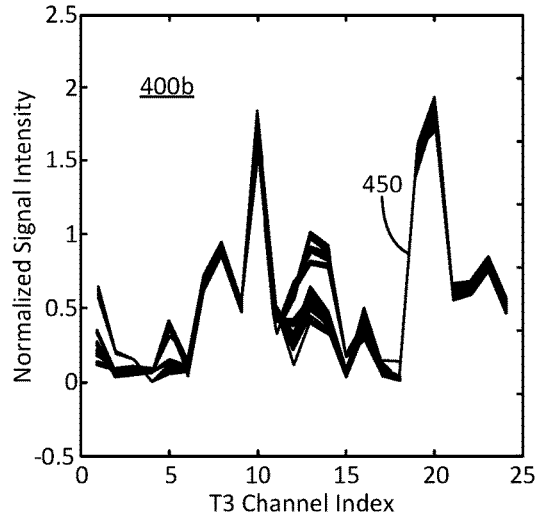
FIG. 4A          FIG. 4B
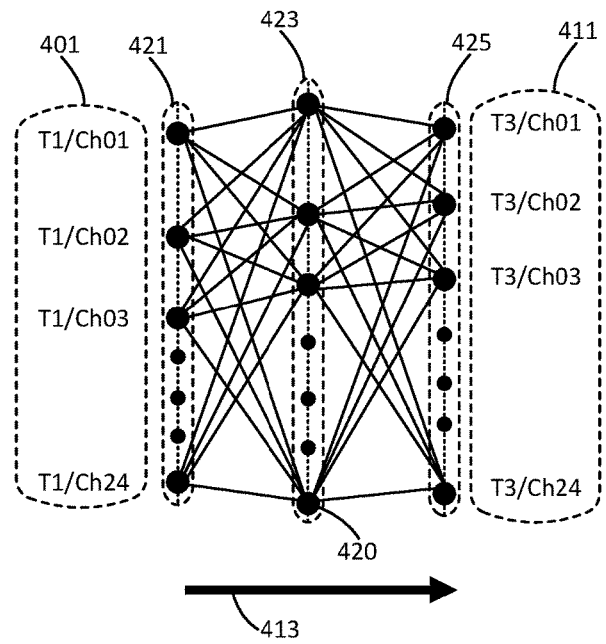
FIG. 4C

SYSTEM AND METHODS FOR CROSS-TOOL OPTICAL FLUID MODEL VALIDATION AND REAL-TIME APPLICATION

BACKGROUND

Real-time estimation of fluid compositions and properties using downhole optical tools is challenging for well testing and sampling in the oil and gas industry. To make real-time fluid analysis, current practice often pre-selects a set of predictive models calibrated in a synthetic database as operational fluid models. However, without using a ruggedized validation method, fluid model pre-selection based on a synthetic calibration database alone may be problematic and curtailed by the limitation of existing databases, especially when a new tool is deployed for the first time in the field. In such cases, problems such as lack of information of signal variation in the real tool system during testing and sampling may occur, and there may be difficulty in using available field data and results in assisting decision making.

Current practice in calibrating fluid predictive models is also sensor dependent. Therefore, field data and results obtained from a particular tool may not be able to validate model selection of other tools in which different optical sensors are used. The issue of data management with individual-sensor-based fluid model calibration may also arise with changes in optical sensor design and updates of calibration databases. Future technology development applied to optical fluid analysis would be hard to implement without data sharing and integration among the tools.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 4A-C illustrate a transformation model calibrated on a data set of reference fluids converting sensor data from a first tool to a second tool in tool parameter space.

In the figures, elements having the same or similar reference numerals refer to the same or similar function, or step, unless otherwise noted.

DETAILED DESCRIPTION

Figure 1:
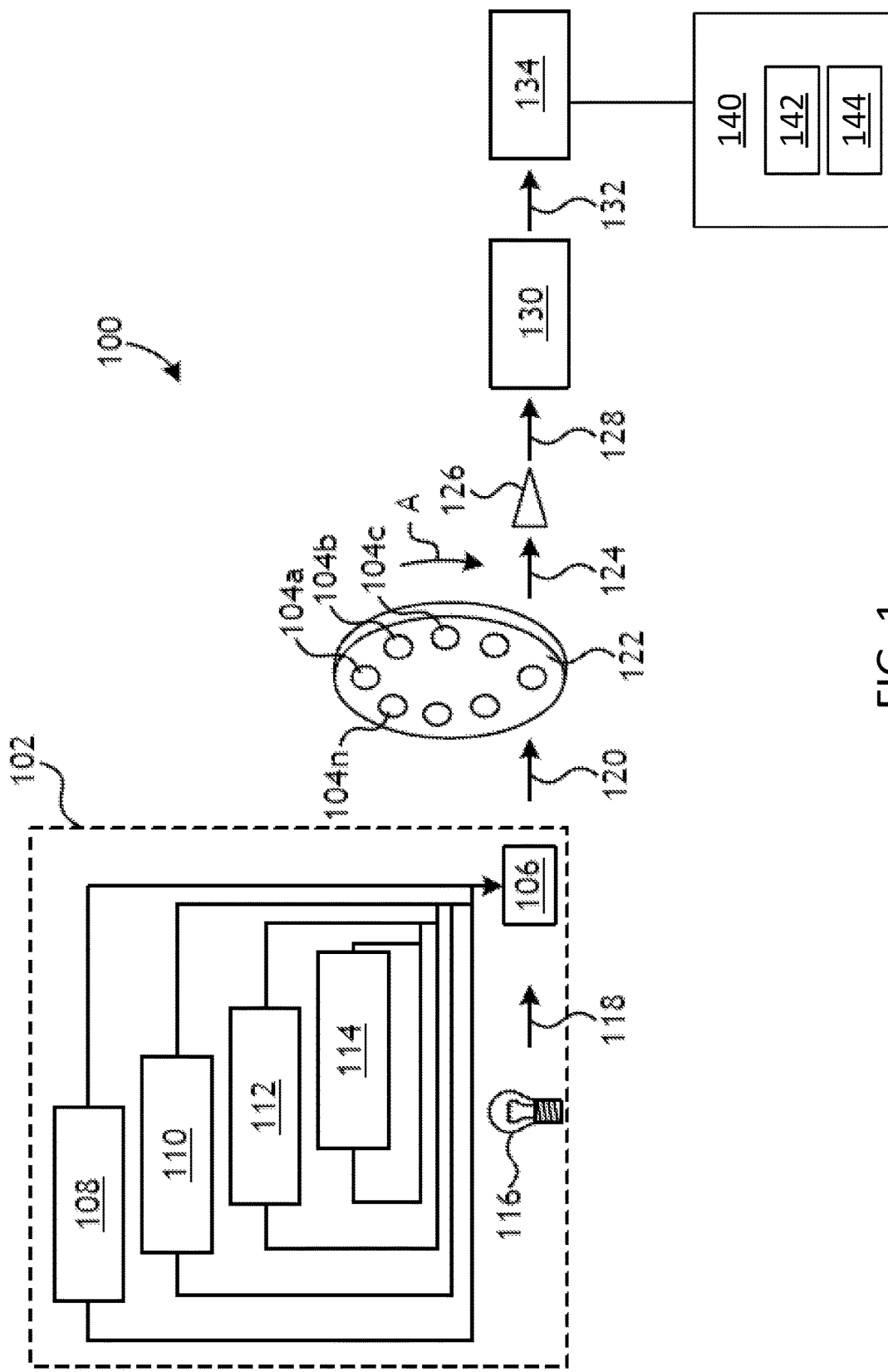
FIG. 1 illustrates a calibration system used to calibrate an optical sensor.

The present disclosure relates to calibration and data processing of optical sensors for downhole optical fluid analysis. More specifically, the present disclosure provides methods for cross-tool optical data transformation as applied to formation fluid validation analysis and real-time software prediction.

This disclosure provides a novel method of sharing and integrating downhole optical fluid measurements obtained in multiple sites around the world with different tools to improve real-time formation fluid characterization and calibration data management. More specifically, this disclosure describes the use of validated field data and results associated with a particular tool or tools from early formation sampling and testing to determine operational fluid model selection of a new tool or whether to adjust operational fluid model selection of an existing tool in estimating fluid compositions and properties. The embodiments described herein can also be used to convert field data from diverse optical sensors to a single or small number of master sensors, thereby reducing cost of fluid model calibration and management of large data sets. Deployment of optical sensors that use the embodiments of the present disclosure may minimize uncertainty of downhole optical fluid analysis, improve quality of services and maximize clients' satisfaction especially when the first field test includes a new tool. Embodiments described herein may also lead to development of the next generation real-time downhole fluid analysis software using a single master-sensor-based calibration.

Tools consistent with the current disclosure may be deployed in a wide variety of conditions regardless of types of fluids and types of optical sensors used in the tools. For example, field data measured with early developed tools can be transformed to the equivalent data responses from new tools including latest sensor designs. Cross-tool data transformation algorithms consistent with the present disclosure are developed for universal formation fluid application. Accordingly, a sensor to be used in a first tool can make its model selection by evaluating transformed known live oil data from a sensor on a second tool that is already deployed and operating. Further, the sensor in the first tool may use transformed known gas sample data from a sensor on a third operating tool to validate its general model selection.

Optical computing devices, also commonly referred to as "opticoanalytical devices," can be used to analyze and monitor a substance in real time. Such optical computing devices will often employ an optical element or optical processing element that optically interacts with the substance or a sample thereof to determine quantitative and/or qualitative values of one or more physical or chemical properties of the substance. The optical element may be, for example, an integrated computational element (ICE), also known as a multivariate optical element (MOE), which is essentially an optical interference-based device that can be designed to operate over a continuum of wavelengths in the electromagnetic spectrum from the UV to mid-infrared (MIR) ranges, or any sub-set of that region. Electromagnetic radiation that optically interacts with a substance is changed and processed by the ICE so as to be readable by a detector, such that an output of the detector can be correlated to the physical or chemical property of the substance being analyzed. Other examples of optical elements may include band-pass filters, notch filters, neutral density filters, beamsplitters, polarizing beamsplitters, prisms, diffraction gratings, Fresnel lenses, and the like.

An ICE (hereafter "ICE core") typically includes a plurality of optical layers consisting of various materials whose index of refraction and size (e.g., thickness) may vary between each layer. An ICE core design refers to the number and thickness of the respective layers of the ICE core. The layers may be strategically deposited and sized to selectively pass predetermined fractions of electromagnetic radiation at different wavelengths configured to substantially mimic a regression vector corresponding to a particular physical or chemical property of interest of a substance. Accordingly, an ICE core design will exhibit a transmission function that is weighted with respect to wavelength. As a result, the output light intensity from the ICE core conveyed to a detector may be related to the physical or chemical property of interest for the substance.

The terms "optical computing device" and "optical sensor" are used herein interchangeably and refer generally to a sensor configured to receive an input of electromagnetic radiation that has interacted with a substance and produced an output of electromagnetic radiation from an optical element arranged within or otherwise forming part of the optical computing device. The processing element may be, for example, an ICE core as described above. Prior to field use, the optical computing device, with each optical element employed therein, is calibrated such that each output response can be used in conjunction with others to calculate fluid composition and properties through various signal transformation and characterization models upon being exposed to downhole conditions. When an optical computing device is not properly calibrated, the resulting models or algorithms, which correlate optical sensor responses to the fluid characteristics of interest, may not be able to provide accurate fluid predictions upon deployment.

After manufacture, and before downhole use, each optical computing device is carefully calibrated against known reference fluids for temperature and pressure ranges expected to be encountered in the field. The measurement data of each sensing element on the given reference fluids form the basis for developing optical signal transformation models. Once selected reference fluids adequately possess representative features of global petroleum and/or formation fluids, the optical signal transformation algorithms calibrated with a variety of structures can be found for a wide range of applications in processing downhole optical tool data.

This disclosure provides a cross-tool optical data transformation method applied to formation fluid validation analysis for pre-job operational fluid model selection and real-time software processing. In some embodiments, the selected pre-existing optical measurements from a field sensor with known results about fluid composition and other properties can be mapped into the data space of a second new sensor first using a cross-tool nonlinear or linear data transformation algorithm. Then, a different cross-space data transformation algorithm is applied to the second sensor, which further converts previously mapped optical signals from the sensor parameter space to the fluid model calibration data space. Following that, the candidate fluid predictive models pre-calibrated for the second sensor can be tested in calibration data space with concatenate-transformed field data as inputs to compare each model prediction with known results and validate the second sensor pre-job operational fluid model selection for deployment of real-time data processing software.

In some embodiments, field data from worldwide deployments using different optical tools are transformed into a validated calibration data space of a single master sensor and processed with single set of fluid models for real-time downhole fluid analysis. The validated field data can be merged into a single master sensor database and grown into a large collection of data with diverse laboratory samples and field samples for optical fluid characterization. Using a single master sensor database may significantly reduce the cost for fluid model calibration and future data management. Methods consistent with some embodiments also include simulating optical fluid responses of different new sensors directly from the measurement data of field sensors in other tools without requiring specific knowledge of the theoretical fluid spectroscopy of each simulated fluid.

Field optical tool measurements obtained from downhole fluid sampling are important to a formation fluid analysis. The factors that may have strong impact on the quality of fluid prediction (e.g., fluid composition and fluid characteristics) could be induced by variation in tool measurement system such as pumping rate, transient status in flow line, tool vibration, firmware change, condition of optical elements, fluid contamination level and other testing conditions. A fluid predictive model calibration in a synthetic database may not have all these factors under consideration, and the robust real-time fluid prediction then becomes a challenge, especially when a new tool is employed in the field first time without early field data available for operational fluid model validation.

Some embodiments of the present disclosure include a method to convert measured optical responses from a first tool to a second tool when a data mapping algorithm is calibrated with typical representative formation/petroleum fluids using advanced modeling tools and frameworks. For pre-job model validation analysis on a new tool, the verified field data associated with a different tool or tools can be converted from early formation testing and sampling jobs to determine the best operational fluid model selection.

In a first embodiment, a method of cross-tool fluid model validation includes selecting verified field data measured with a first sensor of an existing tool and selecting a second sensor, which is different from a first sensor for validation testing. The method may also include modeling cross-tool optical data transformation in a tool parameter space from the first sensor to the second sensor, and mapping the field data to a second sensor synthetic parameter space. The method may further include evaluating a candidate fluid model prediction of the second sensor with a mapped field data from the first sensor. This may further entail optimizing well testing and sampling operation based on the real-time estimated formation fluid characteristics using a validated fluid model of the second sensor in an operating tool.

In a second embodiment, a method for real-time downhole fluid prediction includes transforming real-time optical measurements from a field sensor to a master sensor in tool parameter space, and mapping the converted master sensor responses from the tool parameter space to the synthetic parameter space. The method further includes applying a synthetic master sensor fluid model for real-time downhole fluid composition and property prediction.

FIG. 1 illustrates an exemplary calibration system 100 that may be used to calibrate one or more optical elements used in an optical sensor. As illustrated, system 100 may include a measurement system 102 in optical communication with one or more optical sensors 104 (shown as 104a, 104b, 104c . . . 104n) that are to be calibrated. Each optical sensor 104a-n may include, without limitation, an optical band-pass filter or a multivariate optical element/integrated computational element (e.g., an ICE core). Measurement system 102 may circulate one or more reference fluids with different chemical compositions and properties (i.e., methane concentration, aromatics concentration, saturates concentration, Gas-Oil-Ratio —GOR—, and the like) through an optic cell 106 over widely varying calibration conditions of temperature, pressure, and density. Thus, optical transmission and/or reflection measurements of each reference fluid in conjunction with each optical element 104a-n may be made at such conditions.

Measurement system 102 may include an optical pressure-volume-temperature (PVT) instrument, and the reference fluids circulated in the measurement system 102 may include representative fluids commonly encountered in downhole applications. System 100 may collect output signals from each optical element 104a-n for each specified reference fluid at varying calibration conditions. In some cases, the reference fluids may include representative fluids that are easy to operate for manufacturing calibration such as: dodecane, nitrogen, water, toluene, 1-5 pentanediol, and two liquid crude oils or fluids with no gas concentration (e.g., dead oil). The crude reservoir oils used as reference fluids may be, for example, global oil library 13 (or "GOL13"), and global oil library 33 (or "GOL33"). In other cases, the reference fluids may include samples of live oils mixed with dead oil and hydrocarbon gas, such as methane for example, and the samples of hydrocarbon gases and/or $CO_2$. Manufacturing calibration of the optical sensor may serve the need of detector output re-scaling or instrument standardization.

Measurement system 102 may vary each reference fluid over several set points spanning varying calibration conditions. To accomplish this, as illustrated, measurement system 102 may include a liquid charging system 108, a gas charging system 110, a temperature control system 112, and a pressure control system 114. The liquid charging system 108 injects reference fluids into the fluid circuit to introduce fluid varying perturbations such that calibrating the optical elements 104a-n will incorporate all the expected compounds found in the particular reference fluid. The gas charging system 110 may inject known gases (e.g., $N_2$, $CO_2$, $H_2S$, methane, propane, ethane, butane, combinations thereof, and the like) into the circulating reference fluids. The temperature control system 112 may vary the temperature of the reference fluid to simulate several temperature set points that the optical elements 104a-n may encounter downhole. Lastly, the pressure control system 114 may vary the pressure of the reference fluid to simulate several pressure set points that the optical elements 104a-n may encounter downhole.

Optic cell 106 is fluidly coupled to each system 108, 110, 112, and 114 to allow the reference fluids to flow therethrough and recirculate back to each of the systems 108, 110, 112, and 114 in a continuous, closed-loop fluid circuit. While the reference fluid circulates through optic cell 106, a light source 116 emits electromagnetic radiation 118 that passes through optic cell 106 and the reference fluid flowing therethrough. As the electromagnetic radiation 118 passes through the optic cell 106 it optically interacts with the reference fluid and generates sample interacted light 120, which includes spectral data for the particular reference fluid circulating through the measurement system 102 at the given calibration conditions or set points. The sample interacted light 120 may be directed toward optical sensors 104a-n which, as illustrated, may be arranged or otherwise disposed on a sensor wheel 122 configured to rotate in the direction A. While shown as arranged in a single ring on the sensor wheel 122, optical sensors 104a-n may alternatively be arranged in two or more rings on the sensor wheel 122. According to embodiments disclosed herein, optical sensors 104a-n may be included in a downhole tool for measurement of a fluid characteristic.

During calibration, sensor wheel 122 may be rotated at a predetermined frequency such that each optical sensor 104a-n may optically interact with the sample interacted light 120 for a brief period and sequentially produce optically interacted light 124 that is conveyed to a detector 126. Detector 126 may be generally characterized as an optical transducer and may comprise, but is not limited to, a thermal detector (e.g., a thermopile), a photo-acoustic detector, a semiconductor detector, a piezo-electric detector, a charge coupled device (CCD) detector, a video or array detector, a split detector, a photon detector (e.g., a photomultiplier tube), photodiodes, and any combination thereof. Upon receiving individually-detected beams of optically interacted light 124 from each optical sensor 104a-n, detector 126 may generate or otherwise convey corresponding response signals 128 to a data acquisition system 130. A data acquisition system 130 may time multiplex each response signal 128 received from the detector 126 corresponding to each optical sensor 104a-n. A corresponding set of resulting output signals 132 is generated and conveyed to a data analysis system 134, for processing and providing input parameters for various fluid predictive models. The fluid predictive models use outputs from each optical element 104a-n as candidate variables.

Data analysis system 134 may be coupled to a computer 140, which may include a memory 142 and a processor 144. Memory 142 may store commands which, when executed by processor 144, cause computer 140 to perform at least some of the steps in the methods described herein and otherwise consistent with the present disclosure.

Once sensor wheel 122 is calibrated, one or more calibrated sensor wheels 122 may then be installed on a downhole tool with other system components, for assembly validation testing. To validate the optical response of the sensor assembly, the sensor may be placed in an oven that regulates the ambient temperature and pressure. The reference fluids used to calibrate sensor wheel 122 may be selectively circulated through the optical sensor at similar set points used to calibrate the optical sensors 104a-n. More particularly, the reference fluids may be circulated through the optical sensor at various set point downhole conditions (i.e., elevated pressures and temperatures) to obtain measured optical responses.

Optical sensors 104a-n are calibrated using the response of the sensors to reference fluids in a tool parameter space. On the other hand, fluid spectroscopic analysis and fluid predictive model calibration using a large amount of data in a standard oil library is performed in a synthetic parameter space (also called Optical-PVT data space). Synthetic sensor responses for each sensor in the downhole tool are calculated as a dot product of full-wavelength-range of fluid spectrometry and sensor element spectrum excited by a light source. The value of the dot product may vary nonlinearly or linearly compared to the actual sensor response due to the difference between the mathematical approximation used in calculating synthetic sensor response and the real system implementation. To compensate for the difference above, the measurement data from the sensors in the downhole tool can be transformed from the tool parameter space to the synthetic parameter space through a reverse transformation algorithm before applying fluid predictive models. In some embodiments, fluid predictive models are calibrated with different synthetic optical inputs, and saved as candidate models in an optical fluid model base. This provides sufficient adaptability in dealing with data transformation uncertainty and improves the formation fluid compositional analysis and field data interpretation.

Figure 2:
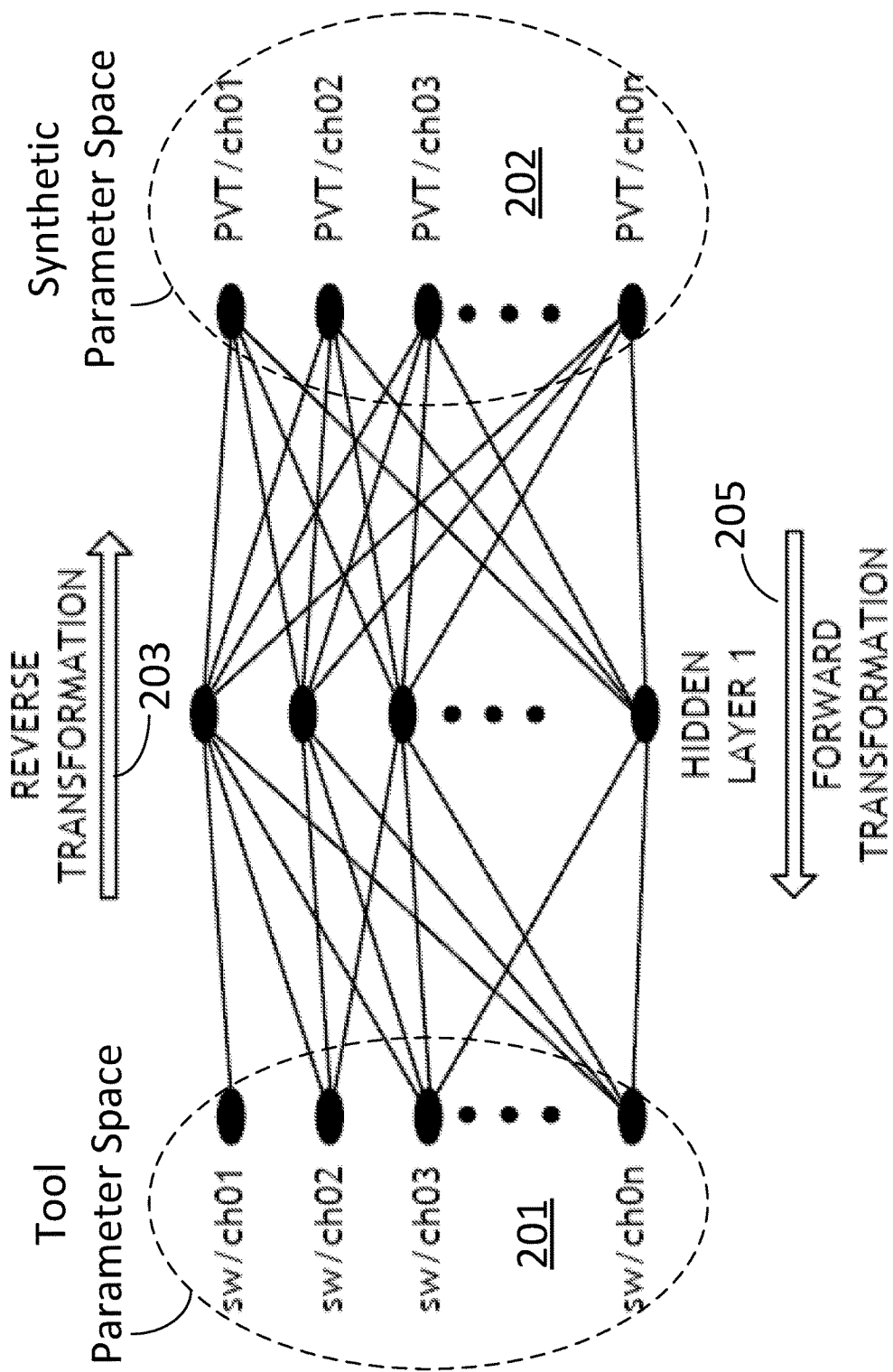
FIG. 2 illustrates a general transformation model framework applied to a forward transformation and a reverse transformation between a tool parameter space and a synthetic parameter space with neural networks.

In current practice, an optical fluid model is dependent on the downhole tool used for measurement. An optical fluid model includes data transformation (i.e., standardization) models and property predictive models. To provide adequate flexibility for optical data processing and interpretation, an optical fluid model includes the following candidate constituents: transformation models calibrated on selected reference fluids through reverse transformation, transformation models calibrated on selected reference fluids through forward transformation, and predictive models calibrated on both Optical-PVT database and sensor wheel 122 data spaces. Depending on the data space in which the fluid property predictive models are calibrated, data transformation models convert measured or simulated optical sensor output between a tool parameter space and a synthetic parameter space. FIG. 2 illustrates one such transformation.

FIG. 2 illustrates an embodiment of a general transformation model framework including a forward transformation 205 and a reverse transformation 203 between data in a tool parameter space 201 and a synthetic parameter space 202 with a non-linear algorithm. In some embodiments, the non-linear algorithm used to implement reverse transformation 203 is a neural network model. In some embodiments, the forward 205 or reverse 203 transformation includes a multi-input, multi-output neural network that may be applied by data analysis system 134 of FIG. 1 to receive inputs and generate outputs of optical sensor responses. The model that converts the actual optical sensor response sensors (SW/Ch01-Ch0n) from tool parameter space 201 to synthetic parameter space 202 (PVT/Ch01-Ch0n) is reverse transformation 203. The model that converts data from synthetic parameter space 202 into tool parameter space 201 is forward transformation 205. Although the illustrated general transformation model framework in FIG. 2 is configured with multi-input/multi-output non-linear neural networks, there is no limitation in using other non-linear and linear transformation algorithms with single-input/single-output and multi-input/single-output configurations.

Figure 3:
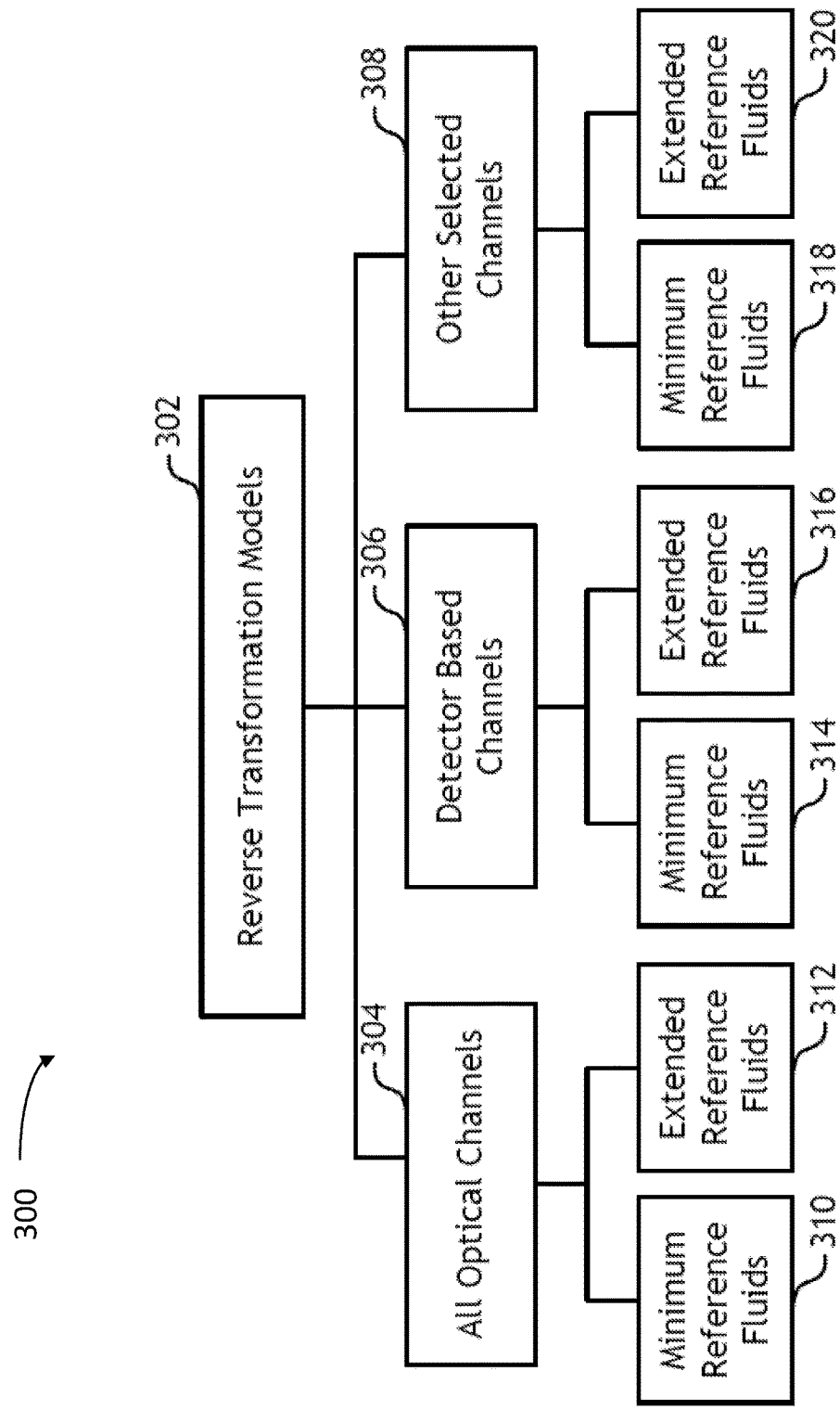
FIG. 3 depicts a hierarchical structure for reverse transformation models.

FIG. 3 illustrates an embodiment of a hierarchical structure for reverse transformation models 302. The variations of transformation models 302 may include converting all sensor responses 304 from each optical element in a single model, converting the disjoined optical elements in several detector-based models 306, or converting only selected sensor elements of interest 308 each time in different individual models. Compared to a single model implementation, multi-model options can improve the reliability of data construction in the output (i.e., transformed) parameter domain (e.g., synthetic parameter space 202, cf. FIG. 2) if one or more of the sensing elements (e.g., tool parameter space 201, cf. FIG. 2), as a transformation input, experience a problem. A plurality of reference fluid blocks 310-320, at the bottom of the hierarchical structure and coupled to the various sensors 304-308, represent the transformation models that can be built based on different reference fluids (e.g., minimum number of reference fluids 310, 314, 318 and extended reference fluids 312, 316, 320). The minimum number of reference fluids may refer to the seven representative fluids discussed above. These reference fluids are safe to use in a laboratory configuration and easy to clean for testing purposes. Optical sensor responses on reference fluids (e.g., tool parameter space 201) generally benefit from a wide dynamic range as a representation of diverse samples in an existing Optical-PVT database and formation fluids. Extended reference fluids often include one or more fluids such as live oil, natural gas and/or gas condensate to provide a more robust transformation model.

In some embodiments, reverse transformation 203 (FIG. 2) converts sensor measurements from tool parameter space 201 into synthetic parameter space 202 prior to applying fluid characterization models. Accordingly, fluid characterization models use synthetic optical sensor responses 202 as input to calculate fluid composition and physical properties. Forward transformation 205 (FIG. 2) can be used to convert a whole set of simulated optical sensor responses from synthetic parameter space 202 to tool parameter space 201 prior to developing predictive models in tool parameter space 201. As seen in FIG. 2, forward transformation 205 can be created by switching the input and the output of a neural network model. In other words, using a synthetic-sensor response as an input and a measured sensor wheel sensor response as an output a neural network can then be trained to calibrate forward transformation algorithms.

As will be appreciated, a hierarchical structure for the reverse transformation models 302, as illustrated in FIG. 3, can also be applied to forward transformation models. After forward transformation 205 is developed, it can be used to convert the synthetic sensor responses of the global samples in synthetic parameter space 202 into tool parameter space 201. Then the fluid property predictive models can be calibrated in tool parameter space 201, and the further transformation is not needed in field data processing because measured optical responses from the sensor can be used as model inputs directly for fluid compositional analysis. Compared to the reverse transformation, which applies on-line sensor data conversion each time before making a fluid prediction, forward transformation usually only applies one time off-line to convert synthetic sensor responses for fluid prediction model development. However, reverse and forward transformations have different complexity with neural network implementation. Compared to a reverse transformation, a forward transformation typically uses a larger number of reference fluids for calibration, and consequently may induce higher uncertainty in fluid model development with use of transformed synthetic database. Therefore, reverse transformation is selected hereafter as general framework for cross-space transformation and used in conjunction with cross-tool transformation described below for operational fluid model validation.

FIGS. 4A-C illustrate a transformation of sensor data in tool parameter space between a first tool data 400a and a second tool data 400b for a data set 450 including a plurality of reference fluids. First tool data 400a may be tool parameter space data from an 'old' tool already deployed in a field application, whereas second tool data 400b may be tool parameter space data from a 'new' tool in calibration for field deployment. Without loss of generality, a sensor having total of twenty four (24) elements or optical channels (from Ch01 to Ch24) 401 are used to collect first tool data 400a and a sensor with same number of twenty four elements 411 are used in second tool data 400b. In some embodiments, the twenty-four sensing elements in each of the first tool and the second tool may include ICE elements and narrow bandpass (NBP) filters, among other optical elements. In general, the optical sensor configuration and element design in first tool data 400a may be different from that in second tool data 400b. For example, data in channel 1 of first tool data 400a may be associated with a methane ICE fabricated according to a first design, and a corresponding data in channel 1 of second tool data 400b may be associated with a methane ICE fabricated according to a second design. Accordingly, the first design may include a first number of alternating dielectric layers, each of the layers having a specific thickness determined according to the first design, and the second design may include a second number of alternating dielectric layers, each of the layers having a specific thickness determined according to the second design. In some embodiments, sensors 401 may include at least one NBP in the ultra-violet (UV)-Visible wavelength domain (approximately from 400 nm to 750 nm), whereas sensors 411 may include at least one NBP in the near-infrared (NIR) wavelength domain (approximately from 750 nm to 2500 nm).

FIG. 4A depicts first tool data 400a that shows optical sensor responses obtained from manufacturing calibration on a plurality of reference fluids, pre-processed on twenty four elements of the first tool, and used as training inputs of a multi-input, multi-output neural network transformation algorithm. Accordingly, the data illustrated in FIG. 4A may be obtained in calibration system 100 (cf. FIG. 1). The abscissae in FIG. 4A include integers indicative of each of the twenty four optical channels 401 in the first tool, and the ordinates indicate a value (intensity) for the signal produced by each element. The value for the signal of each element may include a normalized voltage proportional to an intensity of an interacted light received in a detector from each sensor. Accordingly, each trace having twenty four data points in FIG. 4A corresponds to a reference fluid measured at a setting temperature and pressure in calibration system 100 with sensor 401 from the first tool.

FIG. 4B depicts second tool data 400b that shows optical responses obtained from manufacturing calibration on a plurality of reference fluids, pre-processed on twenty four optical sensor channels 411 (from Ch01 to Ch24) of the second tool, and used as training outputs of a multi-input, multi-output neural network transformation algorithm. Accordingly, the data illustrated in FIG. 4B may be obtained in calibration system 100 (cf. FIG. 1). The abscissae in FIG. 4B include integers indicative of each of the twenty-four optical channels 411 in the second tool, and the ordinates indicate a value for the signal produced by each sensor element. The value for the signal of each sensor element may include a normalized voltage proportional to an intensity of an interacted light received in a detector from each sensor element. Accordingly, each trace having twenty-four data points in FIG. 4B corresponds to a reference fluid measured at a setting temperature and pressure in calibration system 100 with sensor 411 from the second tool.

FIG. 4C shows a cross-tool transformation 413 calibrated to map the data from sensor 401 in first tool data 400a, to data from sensor 411 in second tool data 400b. In some embodiments, transformation 413 is a non-linear mapping such as a multi-input, multi-output neural network (NN) algorithm. The NN algorithm is typically implemented with an input layer 421, a hidden layer 423, and an output layer 425. Input layer 421 receives transformation inputs from sensor 401. Hidden layer 423 has a number of hidden neurons or nodes 420 as adjustable computing elements. In some embodiments, at least one of nodes 420 is equipped with a nonlinear hyperbolic tangent sigmoid or logarithmic sigmoid transfer function to process the weighted linear combinational data from input layer 421 according to a pre-determined transfer function. Output layer 425 is assigned with the same number of elements as sensor 411. The output of each element on output layer 425 is a weighted linear combination of hidden neuron outputs from hidden layer 423.

Figure 5A:
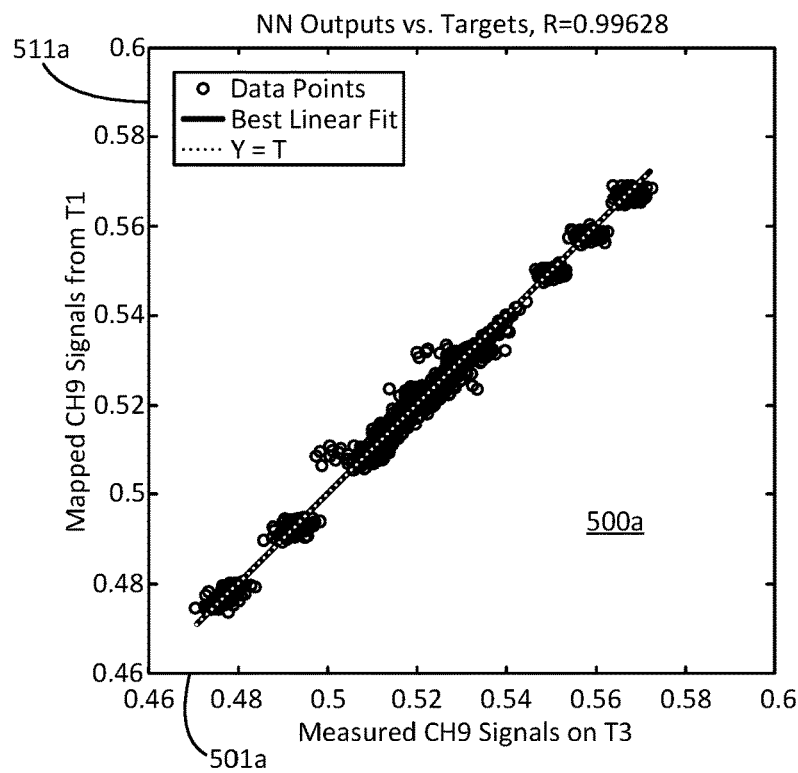
FIGS. 5A-B illustrate the performance of the calibration results for transformation in FIGS. 4A-C comparing model outputs with measured signals for the given optical sensor of the second tool.
Figure 5B:
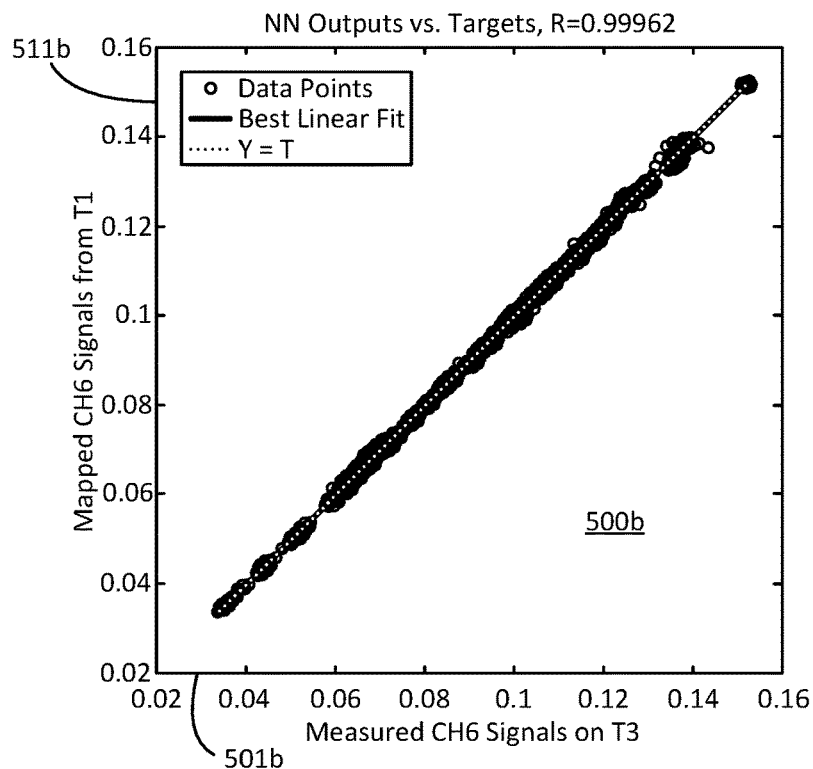

FIGS. 5A-B illustrate the performance of transformation 413 in FIG. 4C comparing simulated signals with measured signals for two optical elements 501a and 501b of second tool data 400b, respectively. Accordingly, the abscissae in FIGS. 5A-B indicate data values for each of the reference fluids measured through a specific sensor element (501a,b) in the second tool (FIG. 4B), and the ordinates in FIGS. 5A-B indicate the data values 511a,b for each of the reference fluids transformed into sensor 501a,b, respectively, from the first tool (FIG. 4A) using transformation 413. Without loss of generality and for illustrative purposes only, sensor 501a is an ICE element corresponding to the ninth sensor channel in second tool data 400b, and sensor 501b is an NBP filter element corresponding to the sixth sensor channel in second tool data 400b.

Thus, in regard to FIG. 5A, the ordinate of a data point in chart 500a is a value obtained for sensor element 501a in the second tool by applying transformation 413 using all of the twenty four optical sensor inputs 401 from the first tool for a reference fluid measured at a setting temperature and pressure. The abscissa of the data point is the measured signal from sensor element 501a in the second tool corresponding to the same reference fluid. The multiple data points in chart 500a may correspond to multiple reference fluids, or to the same reference fluid measured at different PVT conditions in calibration system 100. Likewise, in regard to FIG. 5B, the ordinate of a data point in chart 500b is a value obtained for sensor element 501b in the second tool by applying transformation 413 on all of the twenty four optical sensor inputs 401 from the first tool for a reference fluid measured at a setting temperature and pressure. The abscissa of the data point is the measured signal from sensor element 501b in the second tool corresponding to the same reference fluid. The multiple data points in chart 500b may correspond to multiple reference fluids, or to the same reference fluid measured at different PVT conditions in calibration system 100.

The dispersion of the data points in charts 500a, b around an identity line (X=Y, in charts 500a and 500b) indicates the quality of transformation 413 for cross-tool data transformation algorithm on the reference fluids. In some embodiments, a measure of the quality of the linear approximation as resulting from a plot such as charts 500a, b may be used as a feedback value to train a NN in transformation 413. Accordingly, some embodiments include an iteration of results from transformation 413 to the linearization charts 500a, b such that charts 500a and 500b become as close to the identity as desirable after a number of iterations, or 'training epochs'. More generally, in some embodiments the analysis in charts 500a and 500b for sensor elements 501a and 501b in the second tool may be repeated for more, or all, of the sensor elements in the second tool. In general, note that the number of sensor elements in the first tool data may be the same, smaller, or larger than the number of sensor elements in the second tool.

Figure 6A:
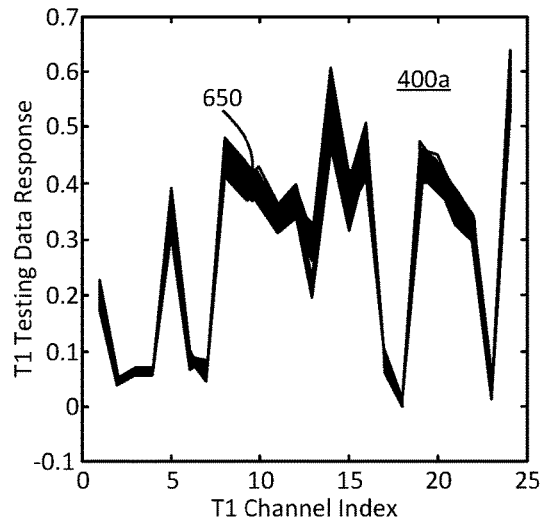
FIGS. 6A-C illustrate a transformation of testing field data in tool parameter space from the first tool to the second tool using the model calibrated in FIGS. 4A-C.
Figure 6B:
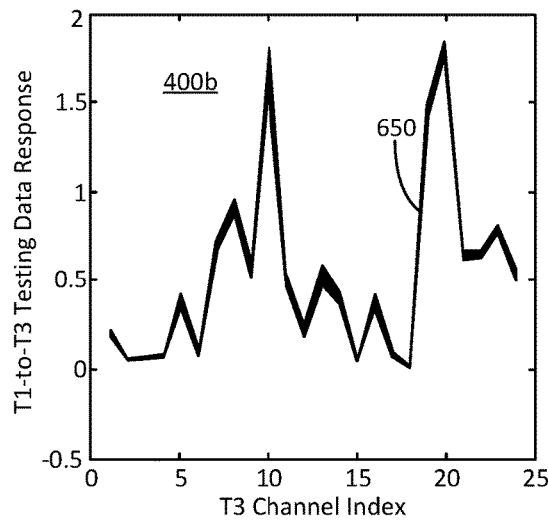
Figure 6C:
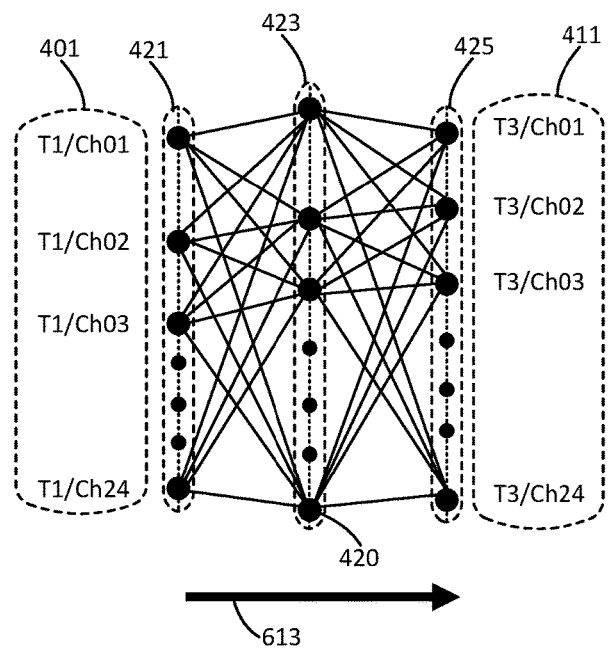

FIGS. 6A-C illustrate a transformation 613 of sensor data in tool parameter space from first tool data 400a to second tool data 400b for a data set 650 including field fluid data measured with the first tool (cf. FIGS. 4A-C). Thus, FIGS. 6A-C are similar to FIGS. 4A-C, except that whereas FIGS. 4A-C include data from reference fluids for calibrating cross-tool transformation algorithm through NN training, FIGS. 6A-C include field data 650 from fluids measured at the downhole by the first tool as an application using calibrated cross-tool transformation algorithm. Accordingly, each of the traces in FIG. 6A corresponds to transformation inputs of a specific fluid measurement by the first tool in the field, and each of the traces in FIG. 6B corresponds to transformation outputs received by the second tool to validate fluid model selection later. In some embodiments, applied transformation 613 is calculated using transformation algorithm calibrated in 413 of FIG. 4C with a minimum number of reference fluids. In other embodiments, transformation 613 may use updated transformation algorithm 413, calibrated with extended number of reference fluids in order to improve fluid model prediction. Note that transformation 613 applied to tool parameter space converts the optical data from the first tool to the second tool. In some embodiments, a fluid predictive model requires inputs from a further transformation, converting data in FIG. 6B to a synthetic parameter space for the second tool, as will be described below. Other elements in FIG. 6C are as described in detail in FIG. 4C, e.g., input layer 421, hidden layer 423 with nodes 420, and output layer 425.

Figure 7A:
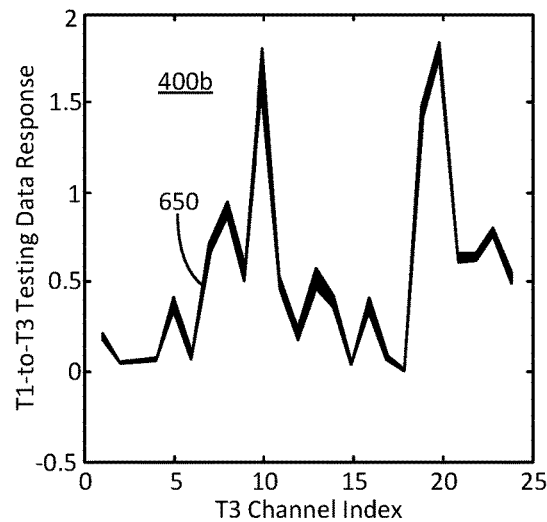
FIGS. 7A-C illustrate a transformation of testing field data from a tool parameter space to a synthetic parameter space for the second tool.
Figure 7B:
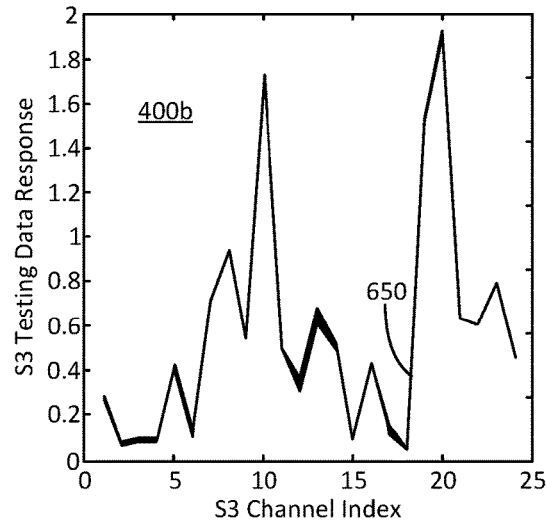
Figure 7C:
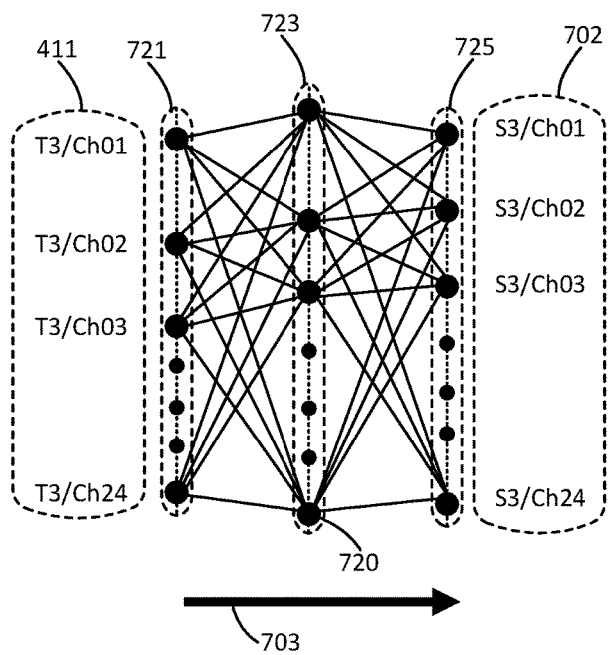

FIGS. 7A-C illustrate a transformation 703 from converted field data 650 in tool parameter space 701 to a synthetic parameter space 702 for the second tool. Field data 650 is associated with fluid data measured in the field with the first tool (cf. FIGS. 6A-C). The abscissae in FIG. 7A include integers indicative of each of the twenty four optical sensor elements in the second tool, and the ordinates indicate a value 411 for the signal produced by each sensor element. The abscissae in FIG. 7B include integers indicative of each of the twenty four optical sensor elements in the second tool, and the ordinates indicate a value 702 for the synthetic signal expected from each sensor element according to a fluid model.

FIG. 7C includes transformation 703 performing a cross-space transformation algorithm, which can be a nonlinear transformation algorithm such as a NN consistent to reverse transformation described in FIG. 2. In some embodiments, cross-space transformation 703 may be obtained by further including same reference fluids for calibration as used in developing cross-tool transformation algorithm (cf. FIGS. 4A-C). Accordingly, cross-space transformation 703 may be a NN including an input layer 721 receiving values 411, a hidden layer 723 having nodes 720, and an output layer 725 providing values in synthetic parameter space 702. In some embodiments, the structure of input layer 721, hidden layer 723, nodes 720, and output layer 725 may be same as the structure of input layer 421, hidden layer 423, nodes 420, and output layer 425, described in detail above (e.g., transformation 413, cf. FIG. 4C). However, although same reference fluids can be used as calibration fluids, the calibration inputs and outputs are different for cross-tool transformation and cross-space transformation. While cross-tool transformation uses measured sensor responses of the first tool as calibration inputs and measured sensor responses of the second tool as calibration outputs in tool parameter space, cross-space transformation uses measured sensor responses of the second tool as calibration inputs and synthetic sensor responses of the second tool as calibration outputs. In embodiments consistent with the present disclosure, transformation 703 is applied at a second concatenation stage of NN transformation that maps data from the tool parameter space of the second tool to the synthetic parameter space of the second tool. Accordingly, concatenating transformation 613 used with transformation 703 enables a direct evaluation of optical fluid models of the second tool using existing field data from the first tool.

In some embodiments, transformation 613 can also be used as a non-linear filter to generate smooth optical inputs for transformation 703. The quality of transformation 703 performed after transformation 613 might even be better than direct transformation 203 (cf. FIG. 2). Because transformation 613 (same as 413) uses hyperbolic tangent sigmoid or logarithmic sigmoid transfer function on hidden layer, the output of each hidden node can be confined to a reasonable range in de-spiking signals on transformation output even the optical sensor inputs are substantially out of the calibration range, especially for mud-filtrate corrupted data. This feature of embodiments consistent with the present disclosure enhances data processing for fluid model validation analysis.

Figure 8A:
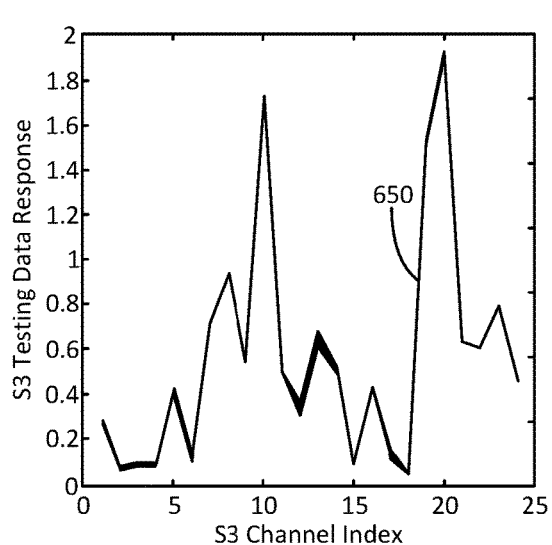
FIGS. 8A-C illustrate a transformation of testing field data from a synthetic parameter space into a fluid characteristic, with a fluid model.
Figure 8B:
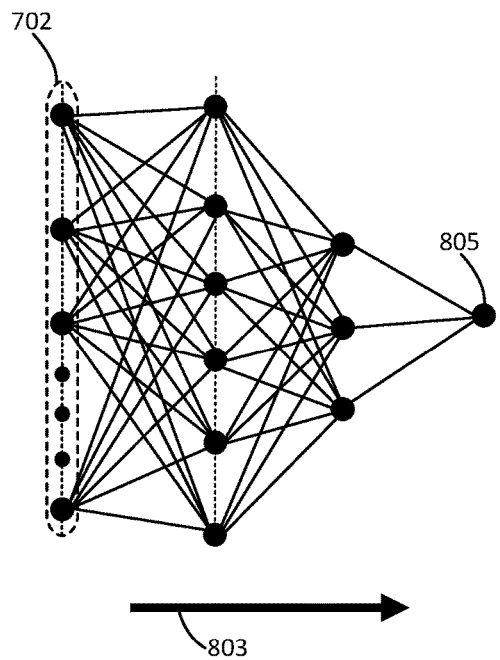
Figure 8C:
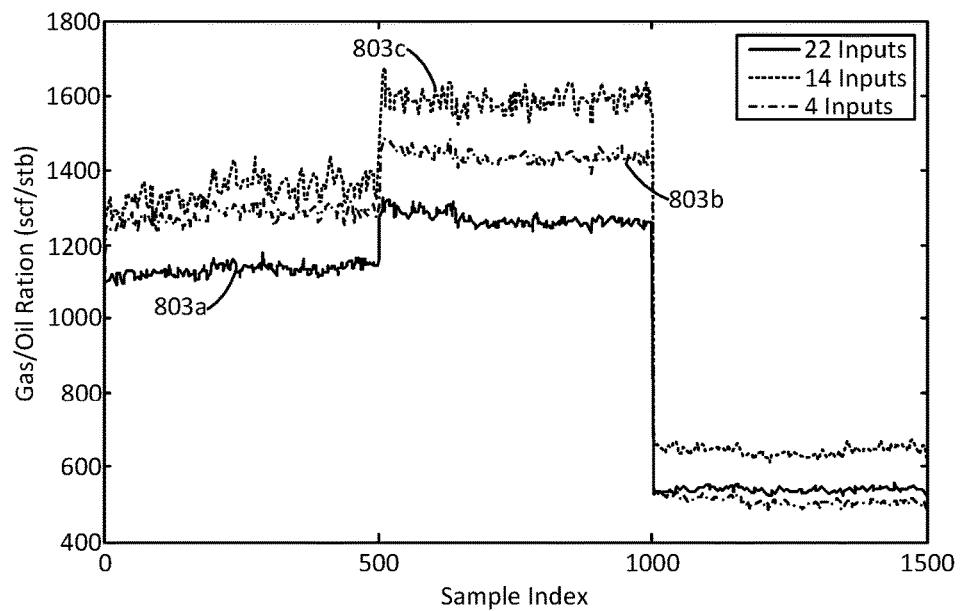

FIGS. 8A-C illustrate a transformation 803 of sensor data from a synthetic parameter space 702 into a fluid characteristic 805, with a fluid model. In FIGS. 8A-C, testing data 650 measured with the first tool is used to evaluate fluid model performance with the second tool (cf. FIGS. 6A-C).

FIG. 8A includes the synthetic parameter space values for field data 650 associated with the second tool according to transformation 703 (cf. FIG. 7B).

FIG. 8B illustrates a transformation 803 from synthetic parameter space values 702 into a fluid characteristic 805 (e.g., GOR) using a nonlinear transformation, such as a NN.

FIG. 8C illustrates a plurality of transformations 803a, 803b, and 803c obtained with sensor-dependent candidate fluid models pre-calibrated in synthetic parameter space 702 with a varying number of sensor inputs, to find an optimal sensor input selection. Without limitation and for illustrative purposes only, transformation 803a includes twenty two (22) sensor channel inputs from the second tool. Transformation 803b includes four (4) sensor channel inputs from the second tool, and transformation 803c includes fourteen (14) sensor channel inputs from the second tool.

FIG. 8C includes a Gas/Oil Ratio (GOR) value in the ordinates. The testing data in the abscissae include three (3) live oil samples with different GOR values (notice the step-like behavior of curves 803a-c, each curve having three different plateaus). Because the results about the fluid composition and properties are known for these samples, the GOR model can be selected from the three candidate transformations 803A-C.

Note that the method and procedure described in FIG. 4A-4C, FIG. 6A-6C, FIG. 7A-7C and FIG. 8A-8C are basically applied for pre-job operational fluid model validation. After the operational fluid model for the second sensor is selected, the optical tool deploying the second sensor can be used for downhole fluid analysis as other existing tools, requiring only cross-space or reverse transformation before applying operational fluid models. However, when the second sensor is a master sensor, it can be used with other tool sensor for real-time data processing by applying concatenate NN cross-tool data transformation, cross-space data transformation and optical fluid identification. Both cross-tool and cross-space NN transformation algorithms are calibrated on a near-complete set of reference fluids to ensure adequate dynamic range for each optical sensor parameter and representative features of formation fluids for quality nonlinear data mapping.

In embodiments consistent with the present disclosure, cross-tool transformation, cross-space transformation and fluid property analysis are not limited to using non-linear neural networks as described above. Different linear data processing and regression algorithms can also apply. Moreover, formation fluid validation analysis is not limited to the example above for GOR prediction. Rather, it may include operational fluid model pre-selection for estimation of many fluid compositions and properties, such as concentrations of methane, ethane, propane, saturates, aromatics, resins, asphaltenes, water and carbon dioxide, and other properties of fluid density and API gravity. The number of candidate models for predicting each analyte could also be different dependent on the available candidate inputs of the optical tool and the chemical complexity of the analyte.

Embodiments consistent with the present disclosure reduce the uncertainty of real-time software prediction in current individual-sensor-based calibration for new optical tools deployed in the field first time. Fluid model pre-selection using validated field measurements through cross-tool optical data transformation algorithm can choose models, which are less sensitive to the tool system variation as default, and produce the robust prediction.

Embodiments consistent with the present disclosure improve post-processing flexibility for quality field data interpretation. Since cross-tool data transformation algorithm has neural network filter functionality, field sensor data can be mapped to a different sensor data space for processing by using less noisy inputs for formation fluid characterization, especially when NN cross-tool data transformation is followed by a linear cross-space data transformation before applying fluid predictive models.

Embodiments consistent with the present disclosure maximize the value of existing large collection of field data when it is shared and used by all tools for formation fluid validation analysis. The current individual-sensor-based fluid model calibration for each tool can be re-evaluated and modified as needed when new field data measured on any tool becomes available.

Embodiments consistent with the present disclosure minimize the cost of fluid model calibration and multi-type data management when master-sensor-based calibration for next generation of real-time data processing software is applied. The calibration file for each new tool can be updated by only re-modeling field-to-master sensor data transformation algorithm without changing master sensor cross-space reverse transformation algorithm and all fluid predictive models. The cost associated with individual-sensor-based calibration therefore can be significantly reduced.

Figure 9:
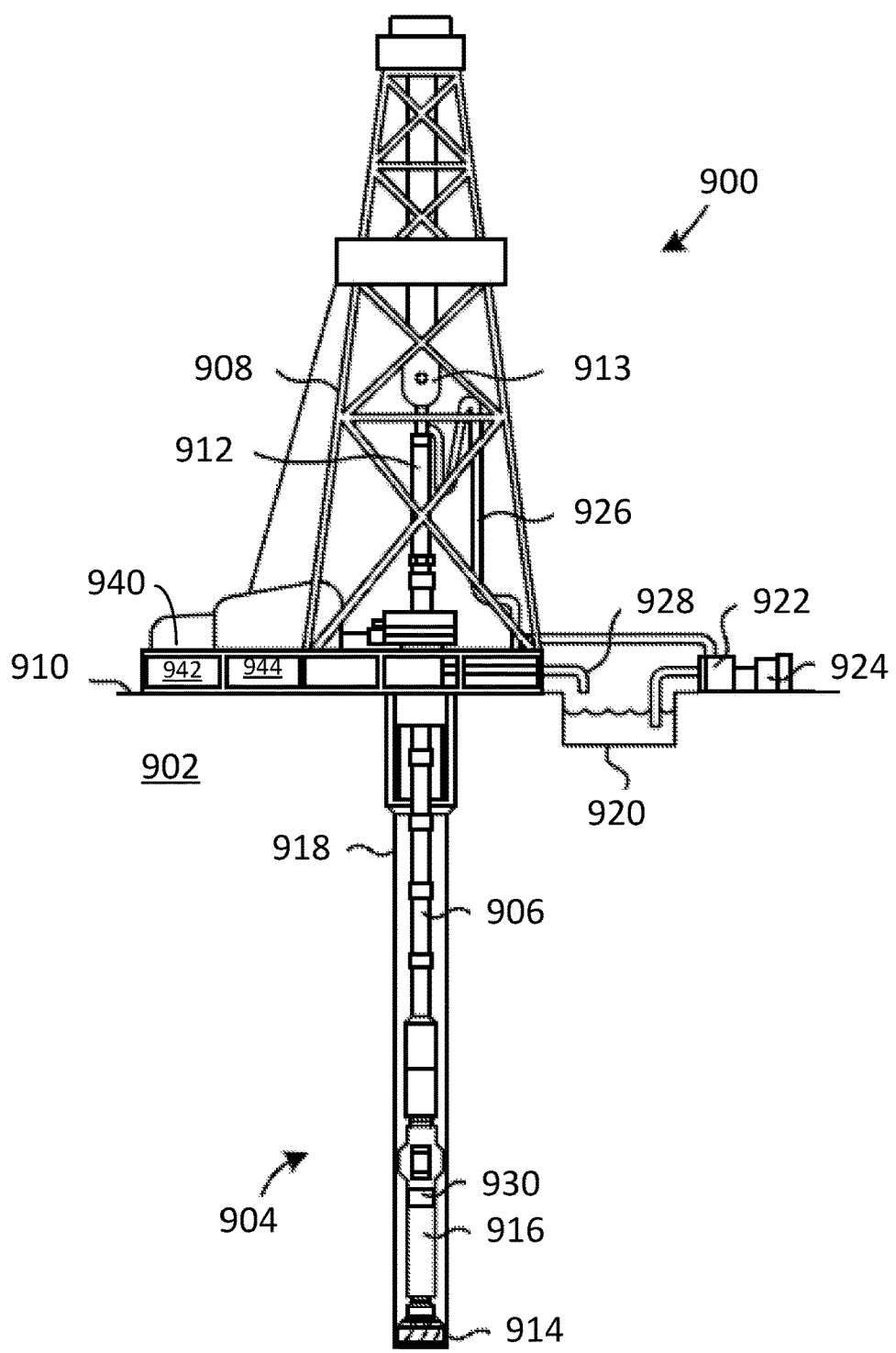
FIG. 9 is a drilling system configured to use a calibrated optical sensor for modifying a drilling parameter or configuration in measurement-while-drilling (MWD) and a logging-while-drilling (LWD) operations.

FIG. 9 is a drilling system 900 configured to use a calibrated optical sensor for modifying a drilling parameter or configuration, such as penetration rate or drilling direction, in a measurement-while-drilling (MWD) and a logging-while-drilling (LWD) operation, according to estimated wellbore or formation fluid properties. Boreholes may be created by drilling into the earth 902 using the drilling system 900. The drilling system 900 may be configured to drive a bottom hole assembly (BHA) 904 positioned or otherwise arranged at the bottom of a drill string 906 extended into the earth 902 from a derrick 908 arranged at the surface 910. The derrick 908 includes a kelly 912 and a traveling block 913 used to lower and raise the kelly 912 and the drill string 906.

The BHA 904 may include a drill bit 914 operatively coupled to a tool string 916 which may be moved axially within a drilled wellbore 918 as attached to the drill string 906. During operation, the drill bit 914 penetrates the earth 902 and thereby creates the wellbore 918. The BHA 904 provides directional control of the drill bit 914 as it advances into the earth 902. The tool string 916 can be semi-permanently mounted with various measurement tools (not shown) such as, but not limited to, measurement-while-drilling (MWD) and logging-while-drilling (LWD) tools, that may be configured to take downhole measurements of drilling conditions. In other embodiments, the measurement tools may be self-contained within the tool string 916, as shown in FIG. 9.

Fluid or "mud" from a mud tank 920 may be pumped downhole using a mud pump 922 powered by an adjacent power source, such as a prime mover or motor 924. The mud may be pumped from the mud tank 920, through a stand pipe 926, which feeds the mud into the drill string 906 and conveys the same to the drill bit 914. The mud exits one or more nozzles arranged in the drill bit 914 and in the process cools the drill bit 914. After exiting the drill bit 914, the mud circulates back to the surface 910 via the annulus defined between the wellbore 918 and the drill string 906, and in the process, returns drill cuttings and debris to the surface. The cuttings and mud mixture are passed through a flow line 928 and are processed such that a cleaned mud is returned down hole through the stand pipe 926 once again.

The BHA 904 may further include a downhole tool 930 similar to the downhole tools described herein. More particularly, downhole tool 930 may have a calibrated optical sensor arranged therein, and the downhole tool 930 may have been calibrated prior to being introduced into the wellbore 918 using the sensor validation testing generally described herein. Moreover, prior to being introduced into the wellbore 918, downhole tool 930 may have been optimized by generally according to the steps illustrated in FIGS. 4A-C, 5A-B, 6A-C, and 8A-C. Downhole tool 930 may be controlled from the surface 910 by a computer 940 having a memory 942 and a processor 944. Accordingly, memory 942 may store commands that, when executed by processor 944, cause computer 940 to perform at least some steps in methods consistent with the present disclosure.

Figure 10:
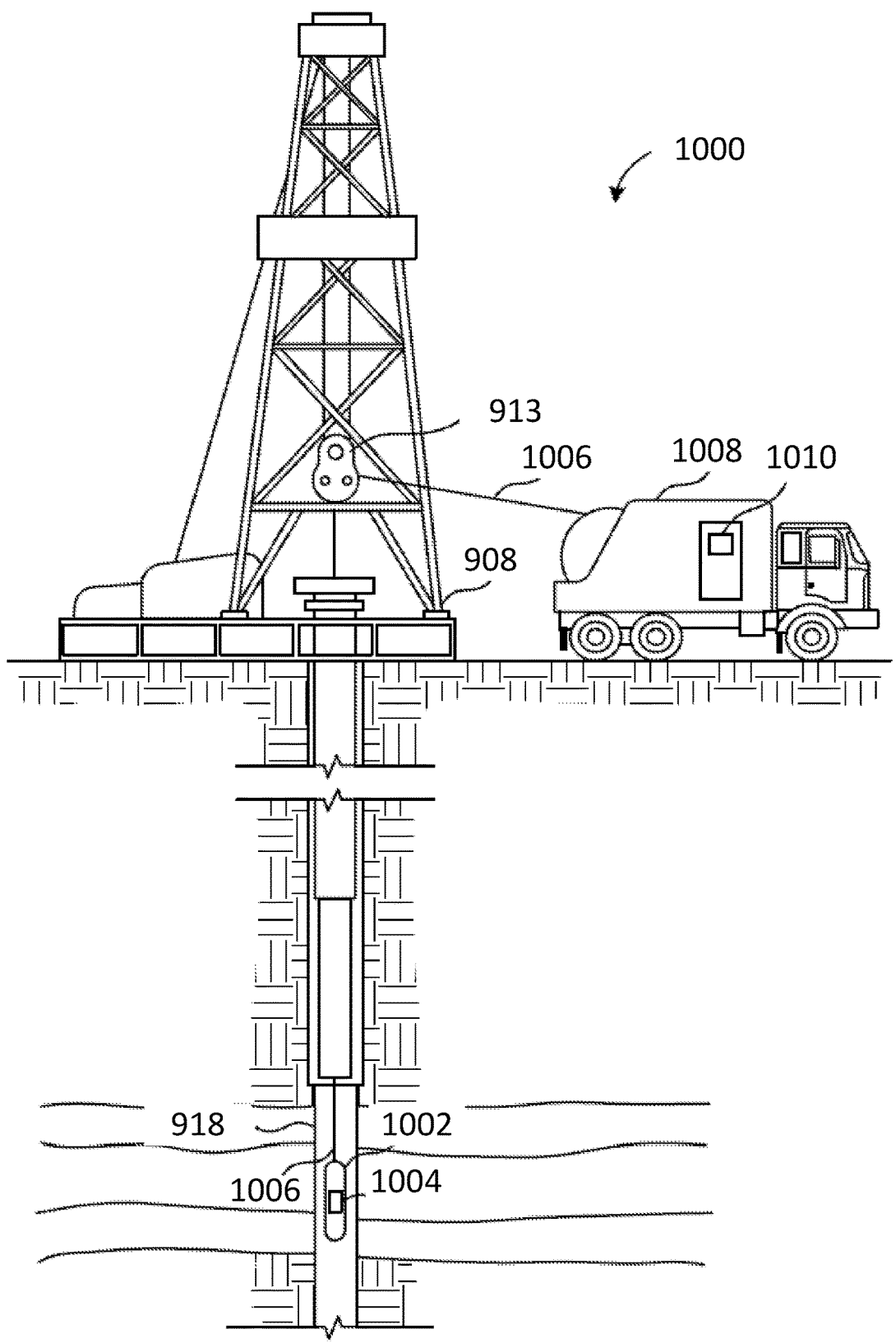
FIG. 10 is a wireline system configured to use a calibrated optical sensor during formation testing and sampling.

FIG. 10 illustrates a wireline system 1000 that may employ one or more principles of the present disclosure. In some embodiments, wireline system 1000 may be configured to use a formation tester and calibrated optical tool. After drilling of wellbore 918 is complete, it may be desirable to know more details of types of formation fluids and the associated characteristics through sampling with use of wireline formation tester. System 1000 may include a downhole tool 1002 that forms part of a wireline logging operation that can include one or more optical sensors 1004, as described herein, as part of a downhole measurement tool. System 1000 may include the derrick 908 that supports the traveling block 913. Wireline logging tool 1002, such as a probe or sonde, may be lowered by wireline or logging cable 1006 into the borehole 918. The tool 1002 may be lowered to potential production zone or the region of interest in the wellbore, and used in conjunction with other components of the formation tester such as packers and pumps to perform well testing and sampling. Sensor 1004 may be configured to measure optical responses of the formation fluids, and any measurement data generated by downhole tool 1002 and its associated optical sensors 1004 can be real-time processed for decision-making, or communicated to a surface logging facility 1008 for storage, processing, and/or analysis. Logging facility 1008 may be provided with electronic equipment 1010, including processors for various types of signal processing.

Figure 11:
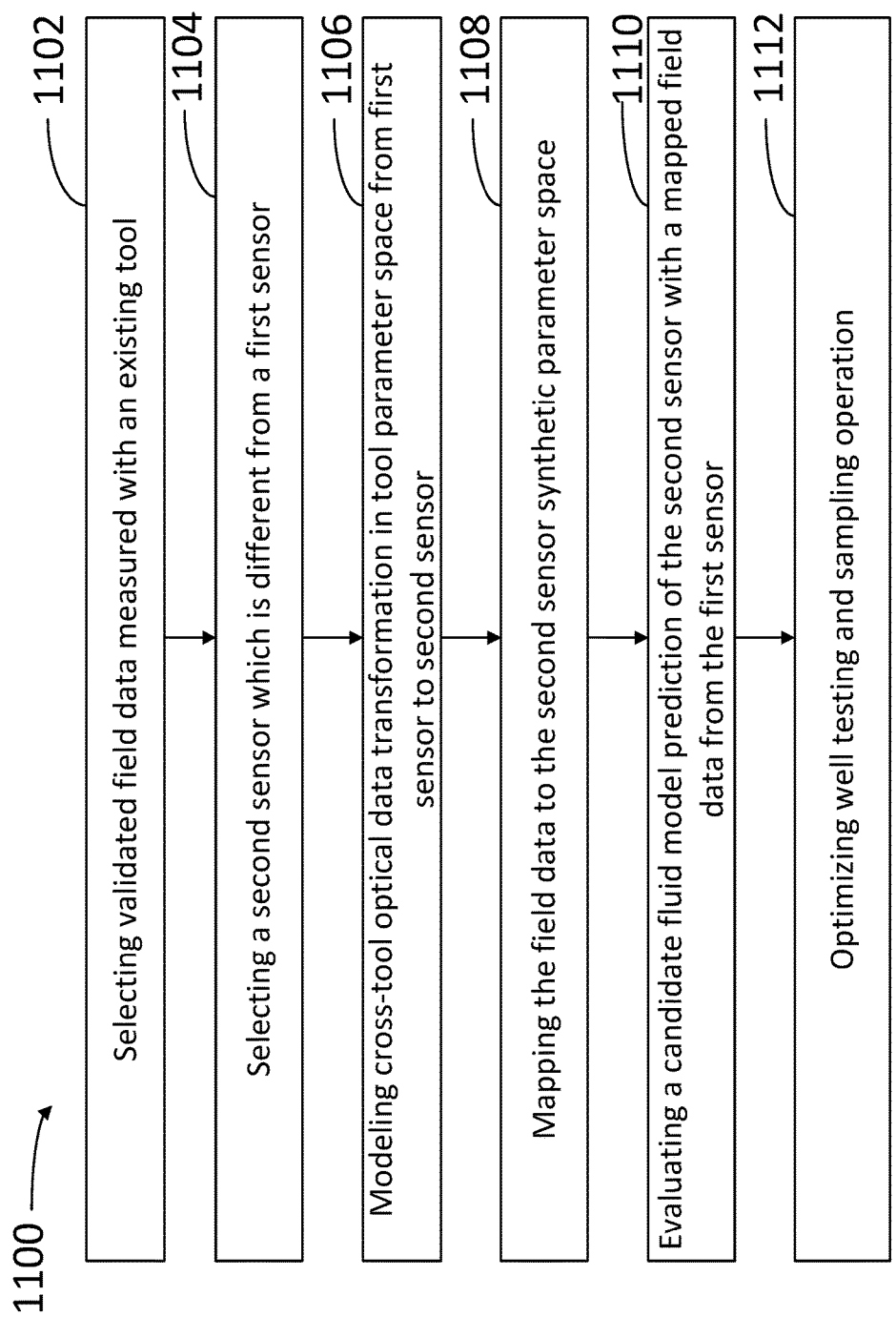
FIG. 11 illustrates a schematic flowchart of a method for optimizing well testing and sampling operation with fluid models of a downhole tool selected from cross-tool validation.

FIG. 11 illustrates a schematic flowchart of a method 1100 for optimizing well testing and sampling operation with fluid models of a downhole tool selected from cross-tool validation method as disclosed herein. In some embodiments, method 1100 may be performed at least partially by a tool calibration system including a plurality of optical sensors to be calibrated with a plurality of reference fluids (e.g., tool calibration system 100 and optical sensors 104, cf. FIG. 1). Further according to some embodiments, steps in method 1100 may be performed with a data analysis system coupled to a computer having a processor and a memory (e.g., data analysis system 134, computer 140, memory 142, and processor 144, or computer 940, memory 942, and processor 944, and logging tool 1008, cf. FIGS. 1, 9 and 10). The data analysis system may perform at least some of the steps in method 1100 when the processor executes commands stored in the memory.

Methods consistent with the present disclosure may include at least some, but not all of the steps illustrated in method 1100, performed in a different sequence. Furthermore, methods consistent with the present disclosure may include at least two or more steps as in method 1100 performed overlapping in time, or almost simultaneously.

Step 1102 includes selecting validated field data measured with a first sensor of an existing tool. The validated field data are optical responses measured from the field sensor associated with clean (contamination free), near clean, or a mixture of fluid samples with known results about the fluid composition and properties. The known results of fluid samples could be obtained from lab analysis or best estimation using existing fluid models of the field sensor. The validated field data can also be the various sets of data measured by the multiple sensors on the different tools. In some embodiments, step 1102 includes selecting optical responses measured with the first sensor associated with one of a contamination free fluid sample, a near clean fluid sample, or a known mixture of fluid samples, and further includes verifying the composition and the properties of the fluid sample. Further, according to some embodiments, step 1102 may include examining the results from either laboratory analysis or best estimation using existing fluid models of the first sensor. Step 1102 may further include selecting validated field data includes retrieving field data from a plurality of sensors in a plurality of existing tools.

Step 1104 includes selecting a second sensor, which is different from the first sensor for validation testing. In some embodiments, step 1104 further includes installing the second sensor on a new tool and selecting operational fluid model prediction for real-time prediction based on the validated results of cross-tool model performance evaluation. In some embodiments, step 1104 includes selecting a sensor already installed on a second existing tool and further evaluating the fluid model prediction by validating a calibration file available for the second sensor in the second existing tool.

Step 1104, includes selecting a second sensor that is different from the field sensor on a new tool, on the existing tool, or a second existing tool. The second sensor can be a sensor to be installed on a new tool with pre-calibrated candidate fluid predictive models available, requiring operational fluid model selection for real-time software prediction. The second sensor can also be the sensor already installed on other existing tool with default calibration file available, requiring further model validation using other verified field data. The second sensor can also be the master sensor selected as a basis to construct integrated database, requiring collection and accumulation of validated field data and lab data.

Step 1106 includes modeling cross-tool optical data transformation in a tool parameter space from the first sensor to the second sensor. In some embodiments, modeling cross-tool optical data transformation includes modeling at least one of a nonlinear multi-input algorithm, multi-output neural network, or a plurality of multi-input, single-output neural networks for transforming data between a tool parameter space in the first sensor and a tool parameter space in the second sensor. In some embodiments, step 1106 includes developing a cross-tool field sensor to second sensor optical data transformation algorithm. In some embodiments, step 1106 may include modeling linear single-input, single-output algorithm, or multi-input, single-output algorithm, or multi-input, multi-output algorithms for transforming data between a tool parameter space in the first sensor and a tool parameter space in the second sensor. Further, according to some embodiments, step 1106 may include including pre-processing a data of one of the plurality of reference fluids by applying one of: a baseline correction, a normalization, and environmental correction.

Step 1108 includes mapping the field optical data to a second sensor synthetic parameter space. The details of step 1108 will be described in FIG. 13.

Step 1110 includes evaluating a candidate fluid model prediction of the second sensor with a mapped field data from the first sensor. Step 1110 may include determining operational model pre-selection for the second sensor to be used in the field; adjusting operational model selection for the second sensor already deployed on a different tool; and evaluating candidate fluid models for the second sensor being chosen as a master sensor. Note that the candidate fluid models for the second sensors are nonlinearly or linearly pre-calibrated in an Optical-PVT global oil database in predicting fluid composition and properties using synthetic optical sensor responses as primary inputs. For the second sensor to be used in the field, operational model pre-selection is conducted by running the transformed testing data over all candidate models and choosing a particular set of models which provide the best matched predictions with known results of the testing data. For the second sensor already deployed on a different tool, adjusting operational model selection is conducted by running the transformed new testing data and early testing data over pre-selected operational fluid models and other candidate models to find the best trade-off solution. For the second sensor being chosen as a master sensor, evaluating candidate fluid models for the master sensor includes verifying transformed field data prediction using existing models, updating fluid model calibration to minimize prediction error on a large collection of lab and field fluid samples.

In some embodiments, step 1110 includes selecting an operational fluid model from the candidate models for the second sensor where the second sensor is deployed for the first time in a second tool. Also, in some embodiments step 1110 includes adjusting an existing operational fluid model for the second sensor using the transformed new data, where the second sensor has been deployed in a second tool. Further, in some embodiments step 1110 includes updating the operational fluid model or candidate models as needed for the second sensor, where the second sensor is designated as a master sensor. Step 1110 may also include evaluating candidate fluid model predictions includes calculating the fluid compositions and properties from the transformed data inputs through pre-calibrated non-linear or linear predictive algorithms in synthetic parameter space for the second sensor and comparing candidate model estimations with known results. In some embodiments, step 1110 further includes selecting an operational fluid model for the second sensor to be used comprises obtaining a fluid prediction in synthetic parameter space. To this effect, step 1110 may include using a plurality of test fluid models and selecting a particular set of test fluid models for the second sensor. In some embodiments, step 1110 includes selecting the particular set of fluid models based on matching the fluid prediction with a known fluid characteristic associated with the transformed optical data. In some other embodiments, step 1110 includes adjusting an existing operational fluid model for the second sensor comprises obtaining a fluid prediction from the transformed optical data by using the existing fluid model and a plurality of test fluid models respectively, and re-selecting a particular set of test fluid models as updated operational fluid model for the second sensor based on matching the fluid prediction with a known fluid characteristic associated with transformed optical data.

In some embodiments, step 1112 includes optimizing well testing and sampling operation based on real-time estimated formation fluid characteristics using a validated fluid model of the second sensor in an operating tool. In some embodiments, step 1112 includes optimizing well testing and sampling operation based on operational fluid model prediction with data from the second sensor in a downhole tool.

Figure 12:
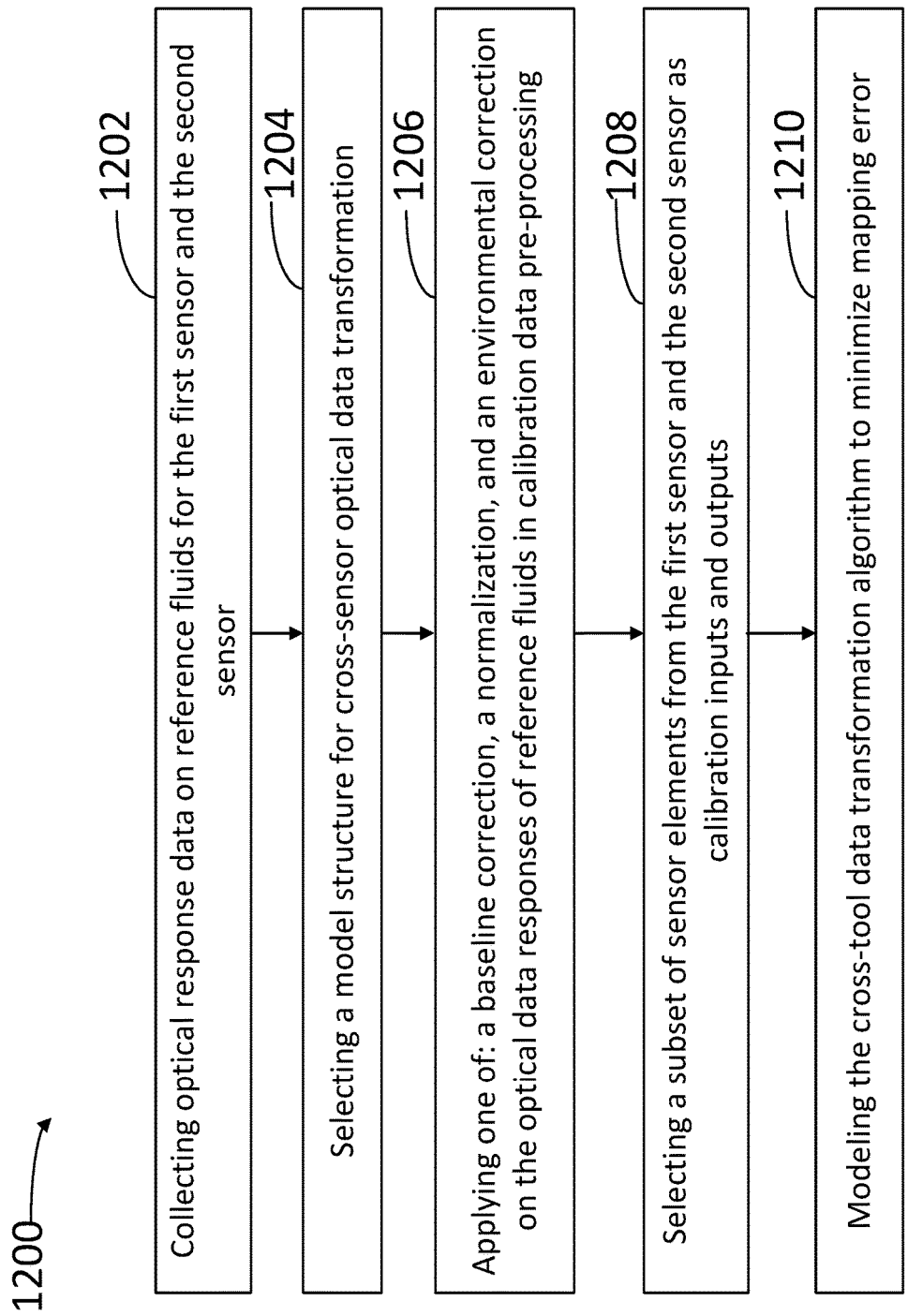
FIG. 12 illustrates a schematic flowchart of a method for modeling cross-tool optical data transformation in tool parameter space.

FIG. 12 illustrates a schematic flowchart of a method 1200 for modeling cross-tool optical data transformation in tool parameter space. In some embodiments, method 1200 may be performed at least partially by a tool calibration system including a plurality of optical sensors to be calibrated with a plurality of reference fluids (e.g., tool calibration system 100 and optical sensors 104, cf. FIG. 1). Further according to some embodiments, steps in method 1200 may be performed with a data analysis system coupled to a computer having a processor and a memory (e.g., data analysis system 134, computer 140, memory 142, and processor 144, or computer 940, memory 942, and processor 944, and logging facility 1008, cf. FIGS. 1, 9 and 10). The data analysis system may perform at least some of the steps in method 1100 when the processor executes commands stored in the memory.

Methods consistent with the present disclosure may include at least some, but not all of the steps illustrated in method 1200, performed in a different sequence. Furthermore, methods consistent with the present disclosure may include at least two or more steps as in method 1200 performed overlapping in time, or almost simultaneously.

Step 1202 includes collecting optical response data on reference fluids for the first sensor and for the second sensor. In step 1202 of FIG. 12, the optical response data on reference fluids measured during manufacturing calibration for both the field sensor and the second sensor is collected. The reference fluids include fluid samples of dead oil, live oil, natural gas and/or gas condensates, water, nitrogen and may be other non-petroleum fluids including, but not limited to toluene, pentanediol and dodecane, to ensure representative features of formation fluids and adequate dynamic range of each optical sensor parameter. The optical responses of the sensor pairs on the selected reference fluids can be obtained from lab testing and/or simulation analysis at matched temperatures and pressures.

Step 1202 may include incorporating the response data from a plurality of reference fluids in the modeling cross-tool optical data transformation. In some embodiments, step 1202 includes selecting a plurality of reference fluids having at least one representative feature of a formation fluid, the plurality of reference fluids providing a wide dynamic range of each optical sensor parameter. In some embodiments, collecting response data from a plurality of reference fluids includes collecting data from at least one of a dead oil sample, a live oil sample, a natural gas and/or gas condensate sample, a water sample, a nitrogen containing sample, or non-petroleum fluids including at least one of: toluene, pentanediol and dodecane. In some embodiments, step 1202 includes incorporating a fluid sample resulting in a low optical sensor response value close or equal to a sensitivity limit of the sensor. Further, in some embodiments, step 1202 includes incorporating a fluid sample resulting in a high and high sensor response value close or equal to a saturation limit of the sensor. Accordingly, in some embodiments step 1202 includes selecting a plurality of fluids providing a dynamic range approximately from a sensitivity limit to a saturation limit of at least one optical sensor element.

Step 1204 includes selecting a model structure for a cross-tool optical data transformation. Candidate model structures in step 1204 may include a nonlinear multi-input, multi-output neural network, or multi-input, single-output neural networks for complex nonlinear mapping. The cross-tool optical data transformation can also be implemented with linear single-input, single-output, or multi-input, single-output, or multi-input, multi-output algorithms for less complicated mapping between the field sensor and the second sensor with consistent configuration and optical element design.

Step 1206 includes applying one of a baseline correction, normalization, an environmental correction on the optical data responses of reference fluids in calibration data pre-processing. Step 1208 includes selecting a subset of sensor elements of interest, if not all, from the first sensor and the second sensor as calibration inputs and outputs. Step 1210 includes modeling the cross-tool data transformation algorithm to minimize mapping error, which further comprises optimizing neural network architecture to adequate complexity and robustness through training for quality data mapping.

Figure 13:
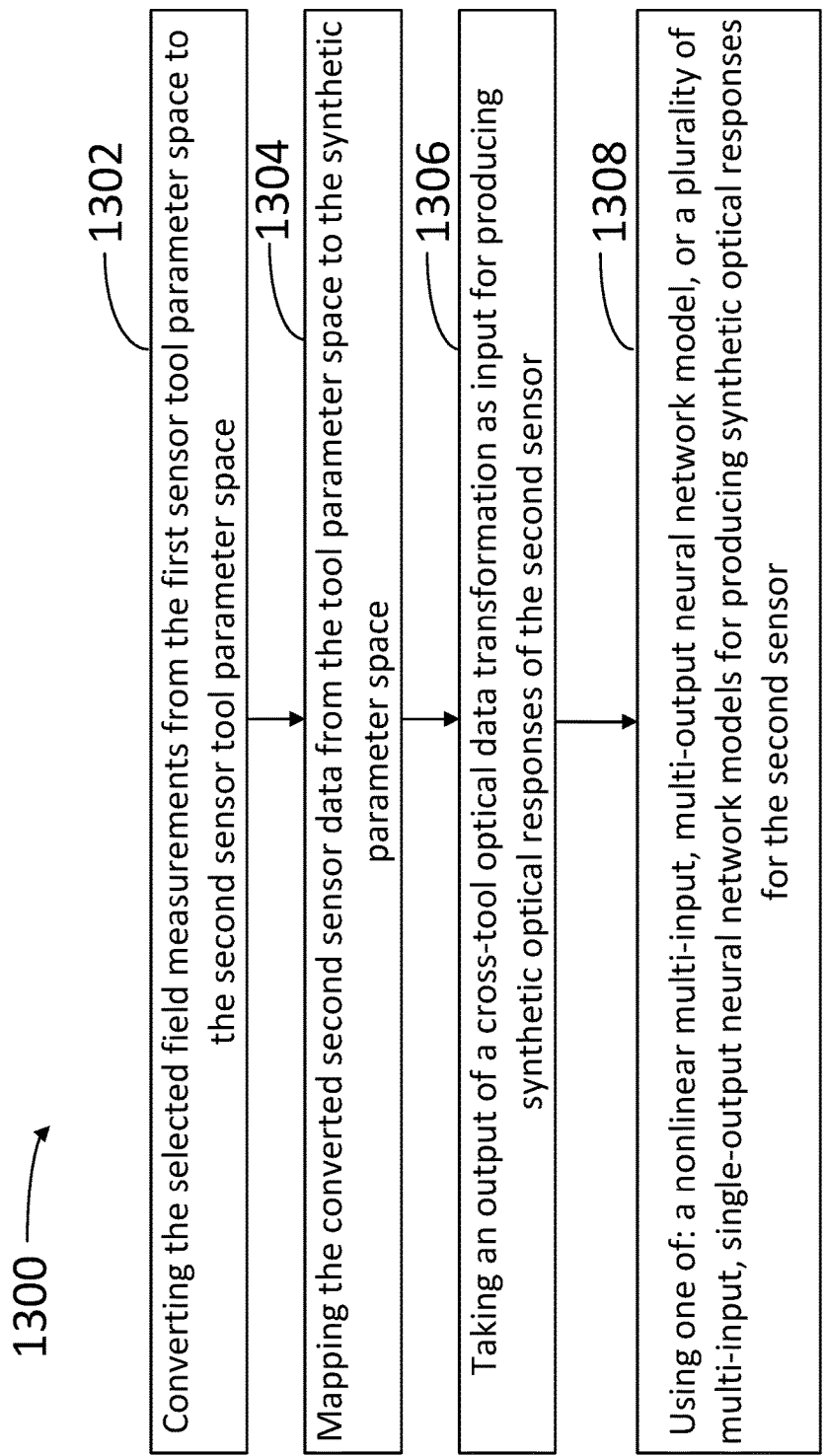
FIG. 13 illustrates a schematic flowchart of a method for mapping a field data from a first tool to the synthetic parameter space of a second tool.

FIG. 13 illustrates a schematic flowchart of a method 1300 for mapping a field data from the first tool to the synthetic parameter space of the second tool. In some embodiments, method 1300 may be performed at least partially by a tool calibration system including a plurality of optical sensors to be calibrated with a plurality of reference fluids (e.g., tool calibration system 100 and optical sensors 104, cf. FIG. 1). Further according to some embodiments, steps in method 1300 may be performed with a data analysis system coupled to a computer having a processor and a memory (e.g., data analysis system 134, computer 140, memory 142, and processor 144, or computer 940, memory 942, and processor 944, and logging facility 1008, cf. FIGS. 1, 9 and 10). The data analysis system may perform at least some of the steps in method 1300 when the processor executes commands stored in the memory.

Methods consistent with the present disclosure may include at least some, but not all of the steps illustrated in method 1300, performed in a different sequence. Furthermore, methods consistent with the present disclosure may include at least two or more steps as in method 1300 performed overlapping in time, or almost simultaneously.

In step 1108 of FIG. 11, the selected field data measured on field sensor or sensors are mapped to the second sensor calibration data space. Step 1108 can be further divided into steps 1302 and 1304 as shown in FIG. 13.

Step 1302 includes converting the selected field measurements from the first sensor to the second sensor tool parameter space. In step 1302, cross-tool optical data mapping from the field sensor to the second sensor is performed in tool parameter space, and calculated through using cross-tool data transformation algorithm with the method described above. The cross-tool data mapping can be applied to full optical sensors or subset of sensors that are consistent with candidate fluid model inputs of the second sensor.

Step 1304 includes mapping the converted second sensor data from the tool parameter space to the synthetic parameter space. In step 1304, cross-space optical data transformation algorithms are used, taking outputs of cross-tool data mapping algorithm as inputs in tool parameter space, and producing synthetic optical responses of the second sensor in fluid model calibration parameter space. The cross-space optical data transformation can be implemented with a nonlinear multi-input, multi-output neural network, or multi-input, single-output neural networks. The cross-space optical data transformation may also be implemented with linear single-input, single-output, or multi-input, single-output, or multi-input, multi-output algorithms.

Step 1306 includes taking an output of the cross-tool optical data transformation as a tool parameter space input for the second sensor and producing synthetic optical responses of the second sensor in synthetic parameter space. Step 1308 includes using one of: a nonlinear multi-input, multi-output neural network model, or a plurality of multi-input, single-output neural network models for producing synthetic optical responses for the second sensor. In some embodiments, step 1308 further includes using one of: a linear multi-input, multi-output model, a plurality of linear single-input, single-output models, or a plurality of multi-input, single-output models, for producing synthetic optical responses for the second sensor.

Figure 14:
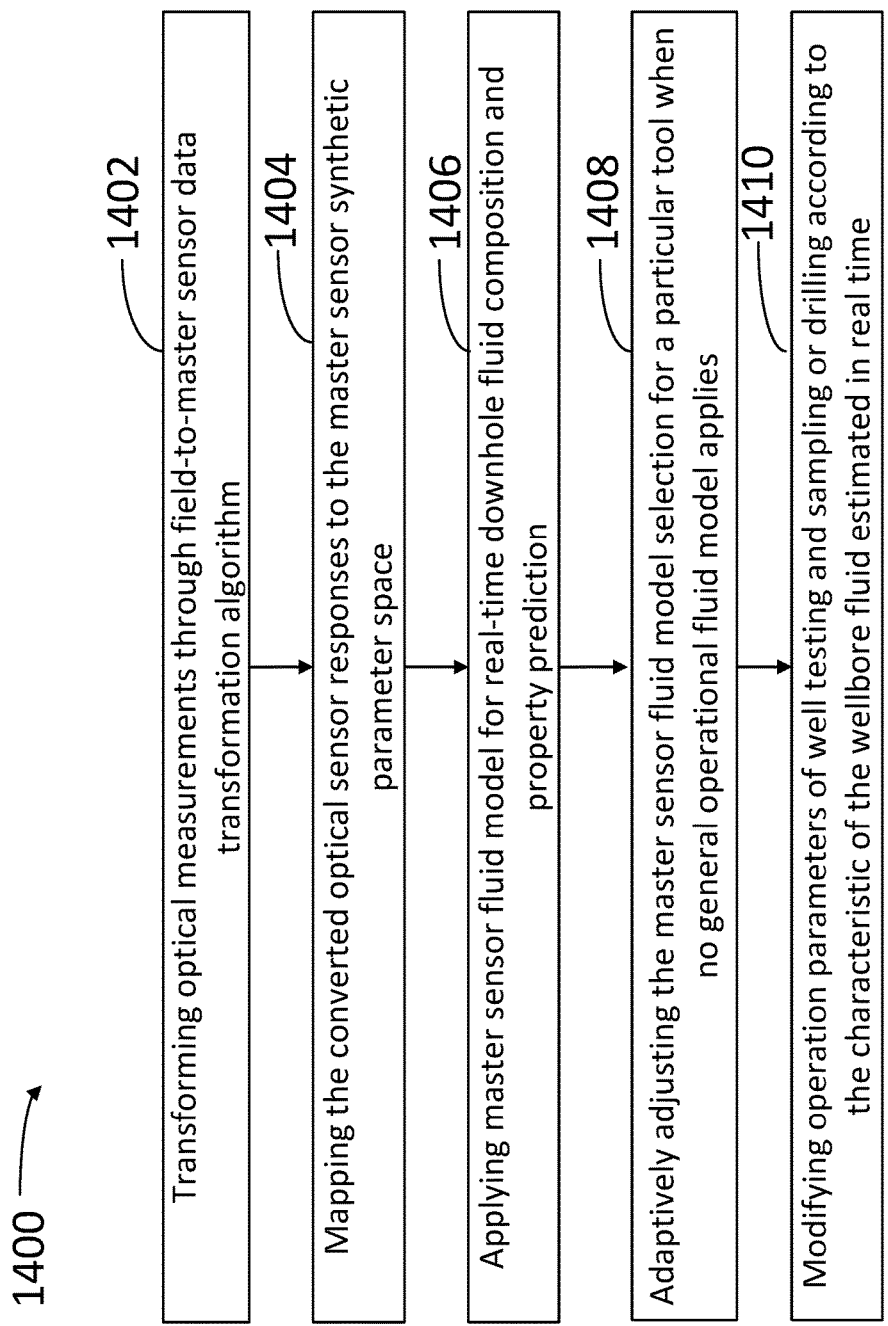
FIG. 14 illustrates a schematic flowchart of a method for mapping a field data from a plurality of field tools to the synthetic parameter space of a master sensor.

FIG. 14 illustrates a schematic flowchart of a method 1400 for mapping a field data from a plurality of field tools to the synthetic parameter space of a master sensor. As a particular application, a single master-sensor-based real-time data processing software may apply in which the optical data measured from different field jobs with different optical tools can be transformed into the validated calibration data space of a single master sensor and processed with single set of fluid models for real-time downhole fluid analysis, as shown in FIG. 14.

In some embodiments, method 1400 may be performed at least partially by a tool calibration system including a plurality of optical sensors to be calibrated with a plurality of reference fluids (e.g., tool calibration system 100 and optical sensors 104, cf. FIG. 1). Further according to some embodiments, steps in method 1100 may be performed with a data analysis system coupled to a computer having a processor and a memory (e.g., data analysis system 134, computer 140, memory 142, and processor 144, or computer 940, memory 942, and processor 944, and logging facility 1008, cf. FIGS. 1, 9 and 10). The data analysis system may perform at least some of the steps in method 1100 when the processor executes commands stored in the memory.

Methods consistent with the present disclosure may include at least some, but not all of the steps illustrated in method 1400, performed in a different sequence. Furthermore, methods consistent with the present disclosure may include at least two or more steps as in method 1400 performed overlapping in time, or almost simultaneously.

The single master-sensor-based calibration in this disclosure could be more attractive for calibration cost reduction. Current individual-sensor-based fluid model calibration involves high cost in measuring each sensor spectra at elevated temperatures and pressures, and updating fluid models with increased fluid samples in database. Master-sensor-based calibration only requires measuring the spectra of a single master sensor for cross-space transformation and building a single set of fluid models for real-time formation fluid analysis. By using cross-tool transformation, the existing manufacturing calibration data on reference fluids can be utilized with no extra cost in building transformation algorithm compared to conventional cross-space data mapping.

The single master-sensor-based calibration of the disclosure would also benefit data management when validated downhole measurements from various optical tools are merged into a single master sensor database and grown into a large collection of data consisting of many lab samples and global field samples. Refining universal predictive models with use of consistently integrated master sensor data would become very convenient for optical fluid analysis, and it would also be very often that only cross-tool transformation model coefficients need to be updated in calibration file for real-time software prediction when a new tool is deployed in the field.

Step 1402 includes transforming optical measurements through field-to-master sensor data transformation algorithm. In some embodiments, selecting a second sensor includes selecting a master sensor, forming a database with data in the synthetic parameter space of the master sensor, and accumulating validated field data and laboratory data in the database.

Step 1404 includes mapping the converted optical sensor responses to the master sensor synthetic parameter space. Step 1406 includes applying master sensor fluid model for real-time downhole fluid composition and property prediction. Step 1408 includes adaptively adjusting master sensor fluid model selection for a particular optical tool as needed when no general operational fluid model applies.

Step 1410 includes modifying the operation parameters of well testing and sampling or drilling according to the characteristic of the wellbore fluid estimated real time.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of I, II, and III" or "at least one of I, II, or III" each refer to only I, only II, or only III; any combination of I, II, and III; and/or at least one of each of I, II, and III.

Embodiments disclosed herein include:

A. A method, including selecting validated field data measured with a first sensor of an existing tool, selecting a second sensor different from the first sensor for validation testing, and modeling a cross-tool optical data transformation in a tool parameter space from the first sensor to the second sensor. In some embodiments, the method includes mapping the field data to a second sensor synthetic parameter space, evaluating a candidate fluid model prediction of the second sensor with a mapped field data from the first sensor, and optimizing well testing and sampling operation based on real-time estimated formation fluid characteristics using a validated fluid model of the second sensor in an operating tool.

B. A method for real-time downhole fluid prediction including transforming real-time optical measurements from a field sensor to a master sensor in tool parameter space, mapping a converted master sensor response from a tool parameter space to a synthetic parameter space, and applying a synthetic master sensor fluid model for real-time downhole fluid composition and property prediction.

Each of the embodiments A and B may have one or more of the following additional elements in any combination:

Element 1, wherein selecting validated field data includes selecting optical responses measured with the first sensor associated with one of a contamination-free fluid sample, a near-clean fluid sample, or a known mixture of fluid samples, and verifying a composition and one or more properties of the contamination-free fluid sample, the near-clean fluid sample, or the known mixture of fluid samples. Element 2, wherein verifying the composition and the properties further includes examining results from one of a laboratory analysis and a best estimation using existing fluid models of the first sensor. Element 3, wherein selecting validated field data includes retrieving field data from a plurality of sensors in a plurality of existing tools. Element 4, further including installing the second sensor on a new downhole tool and selecting an operational fluid model for real-time prediction based on a validated result of a cross-tool model performance evaluation. Element 5, wherein selecting a second sensor includes selecting a sensor already installed on a second existing tool, and wherein evaluating the candidate fluid model prediction includes validating an operational fluid model available for the second sensor in the operating tool. Element 6, wherein selecting a second sensor includes selecting a master sensor, the method further including forming a database with data in a synthetic parameter space of the master sensor, and accumulating validated field data and laboratory data in the database. Element 7, further including selecting a plurality of reference fluids having at least one representative feature of a formation fluid, the optical responses of the plurality of reference fluids providing a dynamic range approximately from a sensitivity limit to a saturation limit of each optical sensor element, collecting a response data from the plurality of reference fluids with the first sensor and with the second sensor, and including the response data from a plurality of reference fluids in a modeling cross-tool optical data transformation. Element 8, wherein collecting the response data from the plurality reference fluids includes collecting data from at least one of a dead oil sample, a live oil sample, a natural gas sample, a water sample, a nitrogen containing sample, and a non-petroleum fluid including at least one of toluene, pentanediol, and dodecane. Element 9, wherein collecting the response data from the plurality of reference fluids includes collecting one of laboratory data or simulated data of a reference fluid, and matching the laboratory data or the simulated data to a pre-determined sample temperature and a pre-determined sample pressure. Element 10, further including pre-processing data of one of the plurality of reference fluids by applying one of a baseline correction, a normalization, and an environmental correction. Element 11, wherein modeling the cross-tool optical data transformation includes selecting a subset of sensing elements in a tool parameter space of the transformation sensor pair. Element 12, wherein modeling the cross-tool optical data transformation includes modeling at least one of a nonlinear multi-input, multi-output neural network, and a plurality of non-linear multi-input, single-output neural networks. Element 13, wherein modeling the cross-tool optical data transformation includes modeling at least one of a linear multi-input, multi-output algorithm, a plurality of linear single-input, single-output algorithms, and a plurality of linear multi-input, single-output algorithms. Element 14, wherein mapping the field data to the second sensor synthetic parameter space includes taking an output of the cross-tool optical data transformation as a tool parameter space input for the second sensor and producing a synthetic optical response of the second sensor in synthetic parameter space. Element 15, wherein producing the synthetic optical response of the second sensor in synthetic parameter space includes using one of: a nonlinear multi-input, multi-output neural network model, or a plurality of nonlinear multi-input, single-output neural network models. Element 16, wherein producing the synthetic optical response of the second sensor in synthetic parameter space includes using one of: a linear multi-input, multi-output model, a plurality of linear single-input, single-output models, or a plurality of linear multi-input, single-output models. Element 17, wherein evaluating a candidate fluid model prediction of the second sensor with a mapped field data as validation fluids includes selecting a new operational fluid model for the second sensor from the performance evaluation of the candidate fluid model on the validation fluids, adjusting an existing operational fluid model for the second sensor based on the candidate model predictions on the validation fluids, and updating candidate fluid models for the second sensor according to the testing results on the validation fluids. Element 18, wherein evaluating the candidate fluid model prediction further includes calculating a fluid composition and one or more properties from a transformed data input through pre-calibrated non-linear or linear predictive algorithms in synthetic parameter space for the second sensor, and comparing the candidate fluid model prediction with known results. Element 19, wherein selecting the new operational fluid model for the second sensor includes obtaining a fluid prediction in synthetic parameter space using a plurality of test fluid models, and selecting a particular set of test fluid models for the second sensor based on matching the fluid prediction with a known fluid characteristic associated with the transformed data input. Element 20, wherein adjusting the existing operational fluid model for the second sensor includes obtaining a fluid prediction from the transformed data input by using a current fluid model and a plurality of test fluid models respectively, and re-selecting a particular set of test fluid models as updated operational fluid model for the second sensor based on matching the fluid prediction with a known fluid characteristic associated with the transformed optical data.

What is claimed is:

1. A method comprising:
   selecting validated field data measured with a first sensor of an existing tool;
   selecting a second sensor in an operating downhole tool, the second sensor being different from the first sensor for validation testing;
   modeling a cross-tool optical data transformation in a tool parameter space from the first sensor to the second sensor;
   mapping the validated field data from the first sensor to a second sensor synthetic parameter space;
   evaluating a candidate fluid model prediction of the second sensor with the mapped validated field data from the first sensor; and
   modifying a well testing and sampling operation performed by the operating downhole tool, the modifying being based on real-time estimated formation fluid characteristics using a validated fluid model of the second sensor in an operating downhole tool, wherein:
   the existing tool is a calibration tool and selecting validated field data measured with the first sensor of the existing tool comprises optically interacting one or more reference fluids with the first sensor through an optic cell in the calibration tool; and
   mapping the validated field data to a second sensor synthetic parameter space comprises transmitting the validated field data to a controller for the operating downhole tool.

2. The method of claim 1, wherein selecting validated field data includes:
   selecting optical responses measured with the first sensor associated with one of a contamination-free fluid sample, a near-clean fluid sample, or a known mixture of fluid samples; and
   verifying a composition and one or more properties of the contamination-free fluid sample, the near-clean fluid sample, or the known mixture of fluid samples.

3. The method of claim 2, wherein verifying the composition and the properties further includes examining results from one of a laboratory analysis and a best estimation using existing fluid models of the first sensor.

4. The method of claim 1, wherein selecting validated field data includes retrieving field data from a plurality of sensors in a plurality of existing tools.

5. The method of claim 1, further including installing the second sensor on a new downhole tool and selecting an operational fluid model for real-time prediction based on a validated result of a cross-tool model performance evaluation.

6. The method of claim 1, wherein selecting a second sensor includes selecting a sensor already installed on a second existing tool, and wherein evaluating the candidate fluid model prediction includes validating an operational fluid model available for the second sensor in the operating downhole tool.

7. The method of claim 1, wherein selecting a second sensor includes selecting a master sensor, the method further including:
   forming a database with data in a synthetic parameter space of the master sensor; and
   accumulating validated field data and laboratory data in the database.

8. The method of claim 1, further including:
   selecting a plurality of reference fluids having at least one representative feature of a formation fluid, optical responses of the plurality of reference fluids providing a dynamic range approximately from a sensitivity limit to a saturation limit of each optical sensor element;
   collecting a response data from the plurality of reference fluids with the first sensor and with the second sensor; and
   including the response data from a plurality of reference fluids in a modeling cross-tool optical data transformation.

9. The method of claim 8, wherein collecting the response data from the plurality reference fluids includes collecting data from at least one of a dead oil sample, a live oil sample, a natural gas sample, a water sample, a nitrogen containing sample, and a non-petroleum fluid including at least one of toluene, pentanediol, and dodecane.

10. The method of claim 8, wherein collecting the response data from the plurality of reference fluids includes collecting one of laboratory data or simulated data of a reference fluid, and matching the laboratory data or the simulated data to a pre-determined sample temperature and a pre-determined sample pressure.

11. The method of claim 8, further including pre-processing data of one of the plurality of reference fluids by applying one of a baseline correction, a normalization, and an environmental correction.

12. The method of claim 1, wherein modeling the cross-tool optical data transformation includes selecting a subset of sensing elements in a tool parameter space of a transformation sensor pair.

13. The method of claim 1, wherein modeling the cross-tool optical data transformation includes modeling at least one of a nonlinear multi-input, multi-output neural network, and a plurality of nonlinear multi-input, single-output neural networks.

14. The method of claim 1, wherein modeling the cross-tool optical data transformation includes modeling at least one of a linear multi-input, multi-output algorithm, a plurality of linear single-input, single-output algorithms, and a plurality of linear multi-input, single-output algorithms.

15. The method of claim 1, wherein mapping the field data to the second sensor synthetic parameter space includes taking an output of the cross-tool optical data transformation as a tool parameter space input for the second sensor and producing a synthetic optical response of the second sensor in synthetic parameter space.

16. The method of claim 15, wherein producing the synthetic optical response of the second sensor in synthetic parameter space includes using one of: a nonlinear multi-input, multi-output neural network model, or a plurality of nonlinear multi-input, single-output neural network models.

17. The method of claim 15, wherein producing the synthetic optical response of the second sensor in synthetic parameter space includes using one of: a linear multi-input, multi-output model, a plurality of linear single-input, single-output models, or a plurality of linear multi-input, single-output models.

18. The method of claim 1, wherein evaluating a candidate fluid model prediction of the second sensor with a mapped field data as validation fluids includes:
   selecting a new operational fluid model for the second sensor from a performance evaluation of the candidate fluid model on the validation fluids;
   adjusting an existing operational fluid model for the second sensor based on the candidate model predictions on the validation fluids; and
   updating candidate fluid models for the second sensor according to testing results on the validation fluids.

19. The method of claim 18, wherein evaluating the candidate fluid model prediction further includes:
   calculating a fluid composition and one or more properties from a transformed data input through pre-calibrated non-linear or linear predictive algorithms in synthetic parameter space for the second sensor; and
   comparing the candidate fluid model prediction with known results.

20. The method of claim 18, wherein selecting the new operational fluid model for the second sensor includes obtaining a fluid prediction in synthetic parameter space using a plurality of test fluid models, and selecting a particular set of test fluid models for the second sensor based on matching the fluid prediction with a known fluid characteristic associated with the transformed data input.

21. The method of claim 18, wherein adjusting the existing operational fluid model for the second sensor includes:
   obtaining a fluid prediction from the transformed data input by using a current fluid model and a plurality of test fluid models respectively; and
   re-selecting a particular set of test fluid models as updated operational fluid model for the second sensor based on matching the fluid prediction with a known fluid characteristic associated with the transformed optical data.

22. A method for real-time downhole fluid prediction including:
   transforming real-time optical measurements from a field sensor to a master sensor in tool parameter space;
   mapping a converted master sensor response from a tool parameter space to a synthetic parameter space;
   applying a synthetic master sensor fluid model for real-time downhole fluid composition and property prediction; and
   modifying a drilling operation performed by a drilling system based on a characteristic of downhole fluid estimated according to the synthetic master sensor fluid model, wherein:
   the master sensor is part of a calibration tool and mapping a converted master sensor response comprises transmitting the master sensor response from the calibration tool to a controller for the field sensor.

* * * * *